United States Patent [19]
Gueudet et al.

[11] Patent Number: 5,852,044
[45] Date of Patent: Dec. 22, 1998

[54] USE OF NK₁ RECEPTOR ANTAGONISTS FOR PREPARING CARDIO-REGULATORY DRUGS

[75] Inventors: Christiane Gueudet; Vincent Santucci, both of Montpellier; Philippe Soubrie, Saint-Mathieu-de-Treviers, all of France

[73] Assignee: Sanofi, Paris, France

[21] Appl. No.: 845,136

[22] Filed: Apr. 21, 1997

Related U.S. Application Data

[63] Continuation of PCT/FR95/01383 Oct. 19, 1995.

[30] Foreign Application Priority Data

Oct. 21, 1994 [FR] France .................................. 94 12589

[51] Int. Cl.⁶ .................................................. A01N 43/42
[52] U.S. Cl. ......................... 514/317; 514/330; 514/331; 514/640
[58] Field of Search ..................... 514/317, 330, 514/331, 640

[56] References Cited

U.S. PATENT DOCUMENTS 5,242,930  9/1993  Baker et al. ............................. 514/305
5,554,627  9/1996  Lewis et al. ............................. 514/305

FOREIGN PATENT DOCUMENTS 0519040  4/1994  France .

OTHER PUBLICATIONS

Novelli et al., *Il Farmaco*, vol. 48 No. 8, pp. 1021–1049, 1993.

Saigo et al., *Regul. Pept.*, vol. 46, No. 1–2, pp. 293–296, 1993.

Prat et al., *Br. J. Pharmacol.*, vol. 112, No. 1, pp. 250–256, 1994.

Delay–Goyet et al., *Eur. J. Pharmacol.*, vol. 222, No. 2–3, pp. 213–218, 1992.

Abstract to EP 591040 HCAPLUS 1994:323276, 1994.

*Primary Examiner*—Marianne M. Cintins
*Assistant Examiner*—Dwayne C. Jones
*Attorney, Agent, or Firm*—Bacon & Thomas, PLLC

[57] ABSTRACT

The invention relates to the use of NK₁ receptor antagonists for the preparation of drugs with a cardioregulatory action, intended in particular for controlling heart rate disorders and cardiac dysrhythtmia.

5 Claims, No Drawings

USE OF NK₁ RECEPTOR ANTAGONISTS FOR PREPARING CARDIO-REGULATORY DRUGS

This application is a continuation of International Application Number PCT/FR95/01383, filed Oct. 19, 1995.

The present invention relates to a novel use of $NK_1$ receptor antagonists.

More particularly, the invention relates to the use of $NK_1$ receptor antagonists for the preparation of drugs with a cardioregulatory action.

In the present description, drugs with a cardioregulatory action are to be understood as meaning drugs for controlling heart rate disorders and cardiac dysrhythmia, particularly disorders caused by pain or stress.

In recent years, numerous research studies have been carried out on tachykinins and their receptors. Tachykinins are distributed throughout both the central nervous system and the peripheral nervous system. The tachykinin receptors have been recognized and are classified into three types: $NK_1$, $NK_2$, $NK_3$. Substance P (SP) is the endogenous ligand of the $NK_1$ receptors, neurokinin A ($NK_A$) that of the $NK_2$ receptors and neurokinin B ($NK_B$) that of the $NK_3$ receptors.

The $NK_1$, $NK_2$ and $NK_3$ receptors have been identified in different species.

A recent review by C. A. Maggi et al. looks at the tachykinin receptors and their antagonists (J. Autonomic Pharmacol., 1993, 13, 23–93).

Neurokinin receptor antagonists are also described in the article by Andrew B. McElroy entitled "Neurokinin Receptor Antagonists" and published in Patent Update 1993, p 1157–1172, and in the article by Russel M. Hagan et al. in Trends Pharmacol. Sci., 1993, 14 315–318.

In the description and the claims which follow, $NK_1$ receptor antagonists, for which substance P is the endogenous ligand, are also referred to as "$NK_1$ antagonists".

Several families of non-peptide $NK_1$ receptor antagonists are described in the following patents in the name of the Applicant: EP-A2-428434, EP-A1-512901, EP-A1-512902, EP-A1-515240, EP-A1-559538 and EP-A1-591040, in the following French patent applications in the name of the Applicant: no. 94 03560, 94 03561 and 94 03701; and in the following documents: EP-A1-0360390, EP-A1-0429366, EP-A2-0436334, EP-A1-0499313, EP-A2-0585913, WO90/05525, WO90/05729, WO91/09844, WO91/18899, WO92/01688, WO92/06079, WO92/20685, WO93/01170, WO93/21155 and WO94/04487.

The following non-peptide compounds may be mentioned very particularly among these antagonists specific for the $NK_1$ receptors: CP-96345 (J. Med. Chem., 1992, 35, 2591–2600), RP-68651 (Proc. Natl. Acad. Sci. USA, 1991, 88, 10208–10212), SR 140333 (Curr. J. Pharmacol., 1993, 250, 403–413), RP-67580 (Mol. Pharmacol., 1994, 45 (3), 500–508), RP-73467 (Bioorg. Med. Chem. Lett., 1994, 4 (5), 669–672), RPR-100893 (Bioorg. Med. Chem. Lett., 1994, 4 (5), 673–676) and CP-99994 (Brit. J. Pharmacol., 1994, Proc. Suppl. 112, 333P).

According to the work of A.W. DUGGAN [Neuropeptides: 1992, 22, 19], it is known that the tachykinin substance P (SP) is released in the dorsal cornua of the spinal cord in response to a nociceptive sensorial stimulation. Furthermore, the work of FLEETWOOD-WALKER et al. [Brain Res., 1990, 519, 169–182] has shown that substance P seems to play an essential part in the transmission of nociceptive information in the central nervous system. Finally, it has been shown that substance P is also involved, via the $NK_1$ receptors, in controlling cardiac function. In this connection, reference may be made to the work of R. COUTURE et al. in Naunyn-Schmiedeberg's Arch. Pharmacol., 1989, 340, 547–557, and that of TSCHOPE et al. in Br. J. Pharmacol., 1992, 107, 750–755.

It has recently been shown that SR 140333, a potent $NK_1$ receptor antagonist, blocks the response of the neurons of the thalamus to nociceptive mechanical stimulation (EMONDS-ALT et al., Eur. J. Pharmacol., 1993, 250, 403–413).

It has now been found that $NK_1$ receptor antagonists antagonize the customary acceleration of the heart rhythm which is due to pain or stress. Thus, according to one of its features, the present invention relates to the use of $NK_1$ antagonists for the preparation of drugs for preventing or controlling the deleterious effects of stress and pain and their pathological consequences, especially in the cardiovascular system; effects which may be mentioned are discomfort, bouts of hypertension, arrhythmia, myocardial infarction and sudden death.

Thus, according to one of its features, the present invention relates to the use of $NK_1$ receptor antagonists for the preparation of drugs with a cardioregulatory action.

The $NK_1$ receptor antagonists which are appropriate for the purposes of the invention are in particular the families of compounds of formulae I to XXIV below.

A first family of $NK_1$ receptor antagonists consists of the aromatic compounds of formula I described in patent application EP-A2-0428434:

$$\begin{matrix} X_1 & X'_1 \\ \diagdown & \diagup \end{matrix} \begin{pmatrix} \phantom{x} \\ \phantom{x} \end{pmatrix} \quad \begin{matrix} Q_1 & R_1 \\ | & | \end{matrix} \quad (I)$$
$$Ar_1-C-Y_1 \quad N-(CH_2)_m C-CH_2-N-T_1-Z_1$$
$$\begin{pmatrix} \phantom{x} \\ \phantom{x} \end{pmatrix} \quad | \\ Ar'_1$$

in which:

m is an integer from 1 to 3;

$Ar_1$ and $Ar'_1$ independently are a thienyl group; a phenyl group which is unsubstituted or monosubstituted or disubstituted by a halogen atom, by a $C_1$–$C_3$-alkyl, by a trifluoromethyl, by an alkoxy in which the alkyl is $C_1$–$C_3$, by a hydroxyl or by a methylenedioxy; or an imidazolyl group, $Ar'_1$ can also be an unsubstituted or halogen-substituted benzothienyl; an unsubstituted or halogen-substituted naphthayl group; a biphenyl group; or an indolyl which is unsubstituted or substituted on the nitrogen by a benzyl group;

$X_1$ is hydrogen;

$X'_1$ is hydrogen or a hydroxyl group or is joined to $X''_1$ below to form a carbon-carbon bond;

or $X_1$ and $X'_1$ together form an oxo group or a dialkylaminoalkoxyimino group of the formula =N—O—$(CH_2)_p$-Am, where p is 2 or 3 and Am is a dialkylamino group, it being possible for each alkyl to contain from 1 to 4 carbon atoms;

$Y_1$ is a nitrogen atom or a group $C(X''_1)$, where $X''_1$ is hydrogen or forms a carbon-carbon bond with $X'_1$;

$Q_1$ is hydrogen, a $C_1$–$C_4$-alkyl group or an aminoalkyl group of the formula $(CH_2)q$-AM', where q is 2 or 3 and Am' is a piperidino, 4-benzylpiperidino or dialkylamino group, it being possible for each alkyl to contain from 1 to 4 carbon atoms;

$R_1$ is hydrogen, a methyl group or a group $(CH_2)_n$-L, where n is an integer from 2 to 6 and L is hydrogen or an amino group;

$T_1$ is a group selected from $$-\overset{O}{\underset{\|}{C}}- \quad \text{and} \quad -\overset{W_1}{\underset{\|}{C}}-NH$$

$W_1$ being an oxygen or sulfur atom; and
$Z_1$ is hydrogen, or $M_1$ or $OM_1$ when $T_1$ is the group $$-\overset{O}{\underset{\|}{C}}-,$$

or $M_1$ when $T_1$ is the group $$-\overset{W_1}{\underset{\|}{C}}-NH-;$$

$M_2$ is hydrogen; a linear or branched $C_1$–$C_6$-alkyl; a phenylalkyl in which the alkyl group comprises from 1 to 3 carbon atoms and which is unsubstituted or monosubstituted or polysubstituted on the aromatic ring by a halogen, a hydroxyl, an alkoxy having 1 to 4 carbon atoms or an alkyl having 1 to 4 carbon atoms; a pyridylalkyl in which the alkyl group comprises from 1 to 3 carbon atoms; a naphthylalkyl in which the alkyl group comprises from 1 to 3 carbon atoms; a pyridylthioalkyl in which the alkyl group comprises from 1 to 3 carbon atoms; a styryl; a 1-methylimidazol-2-ylthioalkyl in which the alkyl group comprises from 1 to 3 carbon atoms; a 1-oxo-3-phenylindan-2-yl; or an unsubstituted, monosubstituted or polysubstituted aromatic or heteroaromatic group;
or one of their salts with mineral or organic acids.

The polycyclic amino compounds of formula II described in patent application EP-A1-0512901 are also appropriate according to the invention:

$$Y_2 \; (b) \; N-(CH_2)_m-C \underset{AR'_2}{\overset{(CH_2)_n}{\underset{(CH_2)_p}{<}}} \overset{Q_2}{\underset{N-T_2-(CH_2)_q-Z_2}{>}} \quad (II)$$

in which:
$Y_2$ is
either a group Cy-N or Cy-$CH_2$—N, in which:
Cy is a phenyl which is unsubstituted or monosubstituted or polysubstituted by a substituent selected from a halogen atom, a hydroxyl, a $C_1$–$C_4$-alkoxy, a $C_1$–$C_4$-alkyl and a trifluoromethyl, said substituents being identical or different; a $C_3$–$C_7$-cycloalkyl group; a pyrimidyl group; or a pyridyl group;
or a group $$Ar_2-(CH_2)_x-\overset{X_2}{\underset{|}{C}}$$

in which:
$Ar_2$ is a phenyl which is unsubstituted or monosubstituted or polysubstituted by a substituent selected from hydrogen, a halogen atom, a hydroxyl, a $C_1$–$C_4$-alkoxy, a trifluoromethyl and a $C_1$–$C_4$-alkyl, said substituents being identical or different; a pyridyl group; or a thienyl group;

x is zero or one; and
$X_2$ is a hydrogen; a hydroxyl; a $C_1$–$C_4$-alkoxy; a $C_1$–$C_4$-acyloxy; a carboxyl; a $C_1$–$C_4$-carbalkoxy; a cyano; a group —$N(X_1)_2$, in which the groups $X_1$ independently are hydrogen, a $C_1$–$C_4$-alkyl, a $C_1$–$C_4$-hydroxyalkyl or a $C_1$–$C_4$-acyl, or -$(X_1)_2$ forms, with the nitrogen atom to which it is bonded, a heterocycle selected from pyrrolidine, piperidine and morpholine; or a group —S—$X_2$, in which $X_2$ is hydrogen or a $C_1$–$C_4$-alkyl group; or $X_2$ forms a double bond with the carbon atom to which it is bonded and with the adjacent carbon atom of the heterocycle;

m is 2 or 3;
$Ar'_2$ is a phenyl which is unsubstituted or monosubstituted or polysubstituted by a substituent selected from a halogen atom, preferably a chlorine or fluorine atom, a trifluoromethyl, a $C_1$–$C_4$-alkoxy and a $C_1$–$C_4$-alkyl, said substituents being identical or different; a thienyl; a benzothienyl; a naphthyl; or an indolyl;
n is 0, 1, 2 or 3;
p is 1 or 2 and, when p is equal to 2, n is equal to 1 and $Q_2$ is two hydrogen atoms;
$Q_2$ is oxygen or two hydrogen atoms;
$T_2$ is a group selected from $$-\overset{C}{\underset{\|}{O}}- \quad \text{and} \quad -CH_2-$$

q is 0, 1, 2 or 3; and
$Z_2$ is a phenyl which is unsubstituted or monosubstituted or polysubstituted by a halogen atom, more particularly a chlorine or fluorine atom, a trifluoromethyl, a $C_1$–$C_4$-alkyl, a hydroxyl or a $C_1$–$C_4$-alkoxy; a naphthyl which is unsubstituted or monosubstituted or polysubstituted by a halogen, a trifluoromethyl, a $C_1$–$C_4$-alkyl or a hydroxyl; a pyridyl; a thienyl; an indolyl; a quinolyl; a benzothienyl; or an imidazolyl; or, when $T_2$ is —C=O, —$(CH_2)_q$-$Z_2$ can also be a benzyl group substituted on the —CH— by a hydroxyl, a $C_1$–$C_4$-alkoxy or a $C_1$–$C_4$-alkyl and optionally substituted on the aromatic ring by a halogen, more particularly a chlorine or fluorine atom, a trifluoromethyl, a $C_1$–$C_4$-alkyl, a hydroxyl or a $C_1$–$C_4$-alkoxy; or an optionally substituted, mono-, di- or tri-cyclic aromatic or heteroaromatic group;
or one of their possible salts with mineral or organic acids, or, when $Y_2$ is $$Ar_2-(CH_2)_x-\overset{X_2}{\underset{|}{C}}$$

one of their quaternary ammonium salts with the nitrogen (b) of the piperidine or an N-oxide derivative with this same nitrogen atom.

The dialkylenepiperidino compounds of formula III described in patent application EP-A1-0512902 constitute another family of $NK_1$ receptor antagonists:

$$Z_3'-T_3'-N \overbrace{\phantom{XXX}} (CH_2)_2-CH-CH_2-\overset{R_3}{\underset{|}{N}}-T_3-Z_3 \quad (III)$$
$$\underset{Ar'_3}{|}$$

in which:

$Ar'_3$ is a phenyl which is unsubstituted or monosubstituted or polysubstituted by a halogen atom, preferably a chlorine or fluorine atom, by a $C_1$–$C_3$-alkyl, by a trifluoromethyl, by a $C_1$–$C_3$-alkoxy or by a hydroxyl; a thienyl, pyridyl or naphthyl group, said groups being unsubstituted or substituted by a halogen, preferably a chlorine or fluorine atom; an indolyl group; or a benzothienyl group;

$R_3$ is hydrogen, a methyl group or a group $(CH_2)_n$-L, where n is an integer from 2 to 6 and L is hydrogen or an amino group;

$Z_3$ and $Z'_3$ independently are a hydrogen atom or a group $M_3$ or $OM_3$; $M_3$ is hydrogen; a linear or branched $C_1$–$C_6$-alkyl; an α-hydroxybenzyl, an α-alkyl-benzyl or a phenylalkyl in which the alkyl group comprises from 1 to 3 carbon atoms and which is unsubstituted or monosubstituted or polysubstituted on the aromatic ring by a halogen, a hydroxyl, an alkoxy having 1 to 4 carbon atoms or an alkyl having 1 to 4 carbon atoms, a pyridylalkyl in which the alkyl group comprises from 1 to 3 carbon atoms; a naphthylalkyl in which the alkyl group comprises from 1 to 3 carbon atoms; a pyridylthioalkyl in which the alkyl group comprises from 1 to 3 carbon atoms; a styryl; a 1-methylimidazol-2-ylthioalkyl in which the alkyl group comprises from 1 to 3 carbon atoms; a 1-oxo-3-phenylindan-2-yl, or an aromatic or heteroaromatic group, said group being unsubstituted or substituted;

$T'_3$ is a bond, a group —$CH_2$— or a group —C(O)—; and $T_3$ is a group selected from

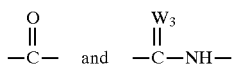

$W_3$ being an oxygen or sulfur atom, with the limitation that
when $Z'_3$ is hydrogen or $OM_3$, $T'_3$ is other than a bond; and
when $Z_3$ is hydrogen or $OM_3$, $T_3$ is other than a group —C($W_3$)—NH; or one of their possible salts with mineral or organic acids or one of their quaternary ammonium salts.

The N-alkylenepiperidino compounds of formula IV described in patent application EP-A1-0515240 are also $NK_1$ receptor antagonists which are suitable for the purposes of the invention:

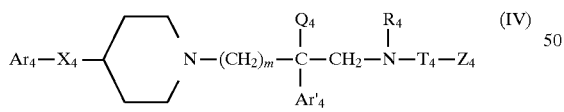

in which:
m is equal to 2 or 3;

$Ar_4$ is a phenyl which is unsubstituted or monosubstituted or polysubstituted by a halogen atom, preferably a chlorine or fluorine atom, by a $C_1$–$C_3$-alkyl, by a trifluoromethyl, by an alkoxy in which the alkyl is $C_1$–$C_3$, by a hydroxyl or by a methylenedioxy; or a thienyl, pyridyl or imidazolyl group which is unsubstituted or substituted by a $C_1$–$C_3$-alkyl, $Ar'_4$ is a phenyl group which is unsubstituted or monosubstituted or disubstituted by a halogen atom, preferably a chlorine or fluorine atom, by a $C_1$–$C_3$-alkyl, by a trifluoromethyl, by an alkoxy in which the alkyl is $C_1$–$C_3$, by hydroxyl or by a methylenedioxy; a thienyl group; an imidazolyl group or a benzothienyl group which are unsubstituted or substituted by a halogen, preferably by a chlorine or fluorine atom; a naphthyl group which is unsubstituted or substituted by a halogen, preferably by a fluorine atom; a biphenyl group; or an indolyl which is unsubstituted or substituted on the nitrogen by a benzyl group;

$X_4$ is an oxygen atom, a sulfur atom, a sulfone, a sulfoxide, a group —NH—, a group

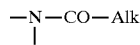

or a group

in which Alk is a $C_1$–$C_3$-alkyl group, or a group

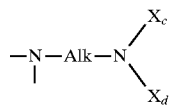

in which Alk is a $C_1$–$C_3$-alkylene and $X_c$ and $X_d$ independently are hydrogen or a $C_1$–$C_3$-alkyl or form, with the nitrogen atom to which they are bonded, a heterocycle selected from pyrrolidine, piperidine and morpholine;

$Q_4$ is hydrogen, a $C_1$–$C_4$-alkyl group or an aminoalkyl group of the formula —$(CH_2)_q$-Am', where q is 2 or 3 and Am' is a piperidino, 4-benzylpiperidino or dialkylamino group, it being possible for each alkyl to contain from 1 to 4 carbon atoms;

$R_4$ is hydrogen, a methyl group or a group $(CH_2)_n$-L, where n is an integer from 2 to 6 and L is hydrogen or an amino group;

$T_4$ is a group selected from

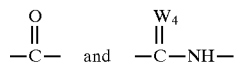

$W_4$ being an oxygen or sulfur atom; and
$Z_4$ is either $M_4$ or $OM_4$ when $T_4$ is the group

or $M_4$ when $T_4$ is the group

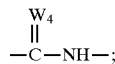

$M_4$ is hydrogen; a linear or branched $C_1$–$C_7$-alkyl; an α-hydroxybenzyl, an α-alkylbenzyl or a phenylalkyl in which the alkyl group comprises from 1 to 3 carbon atoms and which is unsubstituted or monosubstituted or polysubstituted on the aromatic ring by a halogen, a hydroxyl, an alkoxy having 1 to 4 carbon atoms or an alkyl having 1 to 4 carbon atoms; a pyridylalkyl in which the alkyl group comprises from 1 to 3 carbon atoms; a naphthylalkyl in which the alkyl group comprises from 1 to 3 carbon atoms, a pyridylthioalkyl in which the alkyl group comprises from 1 to 3 carbon atoms; a styryl; a 1-methylimidazol-2-ylthioalkyl in which the alkyl group comprises from 1 to 3 carbon atoms; a 1-oxo-3-phenylindan-2-yl; or an unsubstituted, monosubstituted or poly-substituted aromatic or heteroaromatic group;

or one of their salts with mineral or organic acids or one of their quaternary ammonium salts formed with the piperidine nitrogen.

The quaternary salts of 4-substituted piperidines of formula V described in patent application EP-A-0559538 are also $NK_1$ receptor antagonists.

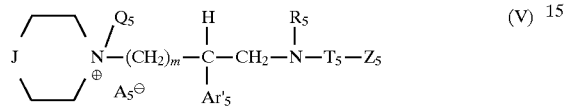

in which:

J is either a group

in which:

Ar$_5$ is a phenyl which is unsubstituted or monosubstituted or polysubstituted by a substituent selected from hydrogen, a halogen atom, a hydroxyl, a $C_1$–$C_3$-alkoxy, a $C_1$–$C_3$-alkyl and a trifluoromethyl, said substituents being identical or different; a $C_3$–$C_7$-cycloalkyl group; a pyridyl group; or a thienyl group;

X$_5$ is hydrogen;

X'$_5$ is hydrogen or is joined to X"$_5$ below to form a carbon-carbon bond, or X$_5$ and X'$_5$ together form an oxo group; and X"$_5$ is hydrogen or forms a carbon-carbon bond with X'$_5$;

*-or a group

in which:

Ar$_5$ is as defined above;

x is zero or one; and

X$_c$ is hydrogen, only when x is zero; a hydroxyl; a $C_1$–$C_4$-alkoxy; a $C_1$–$C_4$-acyloxy; a carboxyl; a $C_1$–$C_4$-carbalkoxy; a cyano; a group —NH—CO-Alk in which Alk is a $C_1$–$C_6$-alkyl; a mercapto group; or a $C_1$–$C_4$-alkylthio group; or X$_c$ forms a double bond with the carbon atom to which it is bonded and with the adjacent carbon atom of the piperidine;

Q$_5$ is a $C_1$–$C_6$-alkyl group or a benzyl group;

A$_5^\ominus$ is an anion selected from chloride, bromide, iodide, acetate, methanesulfonate and paratoluenesulfonate;

m is 2 or 3;

Ar'$_5$ is a phenyl which is unsubstituted or monosubstituted or polysubstituted by a substituent selected from hydrogen, a halogen atom, preferably a chlorine or fluorine atom, a trifluoromethyl, a $C_1$–$C_4$-alkoxy and a $C_1$-$C_4$-alkyl, said substituents being identical or different; a thienyl; a benzothienyl; a naphthyl; or an indolyl optionally N-substituted by a $C_1$–$C_4$-alkyl;

R$_5$ is hydrogen or a $C_1$–$C_6$-alkyl;

T$_5$ is a group selected from

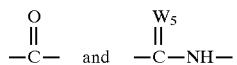

W$_5$ being an oxygen or sulfur atom; and

Z$_5$ is either hydrogen, or M$_5$ or OM$_5$ when T is the group

or M when T is the group

M$_5$ is a $C_1$–$C_6$-alkyl; an α-hydroxybenzyl, an α-hydroxyalkylbenzyl or a phenylalkyl in which the alkyl is $C_1$–$C_3$ and which is optionally monosubstituted or polysubstituted on the aromatic ring by a halogen, a trifluoromethyl, a $C_1$–$C_4$-alkyl, a hydroxyl or a $C_1$–$C_4$-alkoxy; a pyridylalkyl in which the alkyl is $C_1$–$C_3$; a naphthylalkyl in which the alkyl is $C_1$–$C_3$ and which is optionally substituted on the naphthyl ring by a halogen, a trifluoromethyl, a $C_1$–$C_4$-alkyl, a hydroxyl or a $C_1$–$C_4$-alkoxy, a pyridylthioalkyl in which the alkyl is $C_1$–$C_3$; a styryl; or an optionally substituted, mono-, di- or tri-cyclic aromatic or heteroaromatic group.

The quaternary basic amides of formula VI described in patent application EP-A1-0591040 are also antagonists which are appropriate for the purposes of the invention:

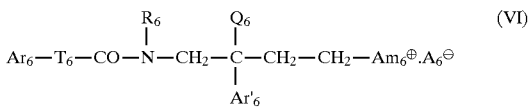

in which:

Ar$_6$ is an optionally substituted, mono-, di- or tri-cyclic aromatic or heteroaromatic group, T$_6$ is a direct bond, a hydroxymethylene group, an alkoxymethylene group in which the alkoxy group is $C_1$–$C_4$, or a $C_1$–$C_5$-alkylene group;

Ar'$_6$ is a phenyl which is unsubstituted or monosubstituted or polysubstituted by a substituent selected from a halogen atom, preferably a chlorine or fluorine atom, a trifluoromethyl, a $C_1$–$C_4$-alkoxy and a $C_1$–$C_4$-alkyl, said substituents being identical or different; a thienyl; a benzothienyl; a naphthyl; or an indolyl;

R$_6$ is hydrogen; a $C_1$–$C_4$-alkyl; ω-($C_1$–$C_4$)alkoxy($C_2$–$C_4$) alkyl; or an ω-($C_2$–$C_4$)alkanoyloxy($C_2$–$C_4$)alkyl;

Q$_6$ is hydrogen or Q$_6$ and R$_6$ together form a 1,2-ethylene, 1,3-propylene or 1,4-butylene group;

Am$_6^\oplus$ is the radical

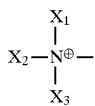

in which X$_1$, X$_2$ and X$_3$, together with the nitrogen atom to which they are bonded, form an azabicyclic or azatricyclic system optionally substituted by a phenyl or benzyl group; and A$_6^\ominus$ is a pharmaceutically acceptable anion.

A compound of formula VI which is particularly preferred for the purposes of the invention is the compound SR 140333 of the formula

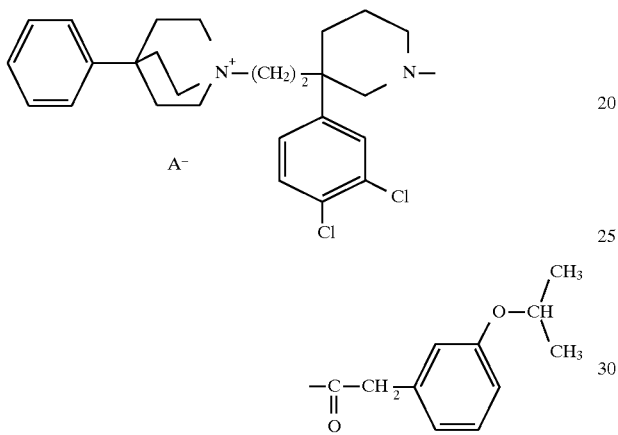

in which A$^-$ is a pharmaceutically acceptable anion such as, for example, chloride, benzenesulfonate, methanesulfonate or p-toluenesulfonate, in particular the chloride and benzenesulfonate salts of (S)-1-{2-[3-(3,4-dichlorophenyl)-1-(3-isopropoxy-phenylacetyl)piperidin-3-yl]ethyl}-4-phenyl-1-azoniabicyclo[2.2.2]octane, called SR 140333 A and SR 140333 B respectively.

The NK$_1$ receptor antagonists of formulae VII, VIII and IX described respectively in patent applications FR94 03561, 94 03560 and 9403701 are also useful for the purposes of the invention.

The compounds according to patent application FR94 03561 are those of formula VII:

$$Ar_7-T_7-CO-N(R_7)-CH_2-\underset{Ar'_7}{\underset{|}{C}(R'_7)}-CH_2-CH_2-Am_7^\oplus \cdot A^\ominus \quad (VII)$$

in which:

Ar$_7$ is:
a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a C$_1$–C$_4$-alkyl; a benzylamino; a carboxyl; a C$_1$–C$_{10}$-alkyl; a C$_3$–C$_8$-cycloalkyl which is unsubstituted or monosubstituted or polysubstituted by a methyl; a C$_1$–C$_{10}$-alkoxy; a C$_3$–C$_8$-cycloalkoxy which is unsubstituted or monosubstituted or polysubstituted by a methyl; a mercapto; a C$_1$–C$_{10}$-alkylthio; an alkylcarbonyloxy in which the alkyl is C$_1$–C$_6$; an alkylcarbonylamino in which the aikyl is C$_1$–C$_6$; a benzoylamino; an alkoxycarbonyl in which the alkoxy is C$_1$–C$_4$; a cycloalkoxy-carbonyl in which the cycloalkyl is C$_3$–C$_7$; a carbamoyl which is unsubstituted or monosubstituted or disubstituted by a C$_1$–C$_4$-alkyl; a ureido which is unsubstituted or monosubstituted or disubstituted in the 3-position by a C$_1$–C$_4$-alkyl or a C$_3$–C$_7$-cycloalkyl; and a (1-pyrrolidino) carbonylamino, said substituents being identical or different;

a naphthyl which is unsubstituted or monosubstituted or polysubstituted by a halogen, a trifluoromethyl, a C$_1$–C$_4$-alkyl, a hydroxyl or a C$_1$–C$_4$-alkoxy; or a pyridyl; a thienyl; an indolyl; a quinolyl; a benzothienyl; or an imidazolyl;

T$_7$ is a direct bond; a hydroxymethylene group; an alkoxymethylene group in which the alkoxy is C$_1$–C$_4$; a C$_1$–C$_5$-alkylene group; an oxygen atom; a group —NR"$_7$–; or a vinylene, Ar'$_7$ is a phenyl which is unsubstituted or monosubstituted or polysubstituted by a substituent selected from a halogen atom, a trifluoromethyl, a hydroxyl, a C$_1$–C$_4$-alkoxy and a C$_1$–C$_4$-alkyl, said substituents being identical or different; a thienyl; a benzothienyl; a naphthyl; or an indolyl optionally N-substituted by a C$_1$–C$_4$-alkyl or a benzyl;

R$_7$ is a hydrogen; a C$_1$–C$_4$-alkyl; an ω-(C$_1$–C$_4$)alkoxy (C$_2$–C$_4$)alkylene; an ω-(C$_1$–C$_4$) alkylcarbonyloxy (C$_2$–C$_4$)alkylene; an ω-hydroxy(C$_2$–C$_4$)alkylene; an ω-(C$_1$–C$_4$) alkylthio(C$_2$–C$_4$)alkylene; an ω-(C$_1$–C$_4$) alkoxycarbonyl(C$_2$–C$_4$)alkylene; an ω-carboxy (C$_2$–C$_4$)alkylene; an ω-(C$_1$–C$_4$)alkylcarbonyl(C$_2$–C$_4$) alkylene or an ω-benzoyloxy(C$_2$–C$_4$)alkylene;

R'$_7$ is hydrogen or R$_7$ and R'$_7$ together form a 1,2-ethylene, 1,3-propylene or 1,4-butylene group;

R"$_7$ is a hydrogen or a C$_1$–C$_4$-alkyl;

Am$_7^\ominus$ is a substituted 1-pyridylium radical of the formula

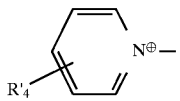

or a substituted 3-thiazolylium radical of the formula

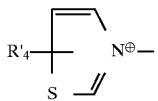

or a substituted 1-pyridazinylium radical of the formula

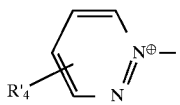

or a substituted 3-imidazolylium radical of the formula

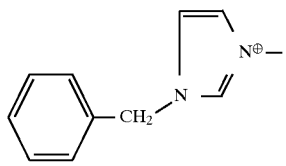

R'$_4$ is a group

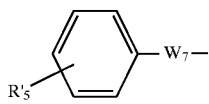

W$_7$ is a direct bond; a methylene group; an oxygen atom; a sulfur atom; or a group —NR"$_7$-;
R'$_5$ is a hydrogen; a halogen; a hydroxyl; a C$_1$–C$_4$-alkoxy; a C$_1$–C$_4$-alkyl; or a trifluoromethyl; and
A$_7^\ominus$ is an anion.

The compounds of formula VII above can be obtained by a process which consists in treating a derivative of the formula

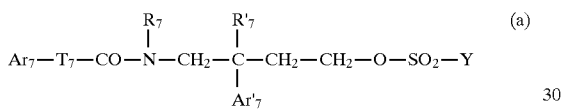 (a)

in which Y is a methyl, phenyl, tolyl or trifluoromethyl group and Ar$_7$, T$_7$, R$_7$, R'$_7$ and Ar'$_7$ are as defined above for (VII), it being understood that when R$_7$ is an ω-hydroxy (C$_2$–C$_4$)alkylene group, the hydroxyl is protected, with an aromatic heterocycle of the formula Am$_7$ (b)

in which Am$_7$ is pyridine substituted by R'$_4$, thiazole substituted by R'$_4$, pyridazine substituted by R'$_4$ or 1-benzylimidazole and R'$_4$ is as defined above for (VII), in an organic solvent, at a temperature between room temperature and 120° C., and, after optional deprotection of the hydroxyl group, the resulting salt is isolated in the form of the sulfonate, or the sulfonate anion (YSO$_3^-$) of the resulting salt is optionally exchanged with another anion, and the optical isomers are optionally separated.

The compounds according to patent application FR94 03560 are the compounds of formula VIII:

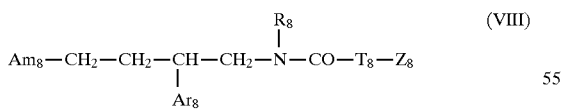 (VIII)

in which:
Am$_8$ is:
    i—either a group Am'$_1$ of the formula

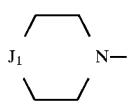

in which J$_1$ is:

i$_1$—either a group

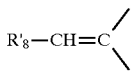

in which R'$_8$ is a phenyl which is unsubstituted or monosubstituted or polysubstituted by a substituent selected from a halogen atom, a hydroxyl, a C$_1$–C$_4$-alkoxy, a C$_1$–C$_4$-alkyl and a trifluoromethyl, said substituents being identical or different, a pyridyl, a thienyl; a pyrimidyl; or an imidazolyl which is unsubstituted or substituted by a C$_1$–C$_4$-alkyl;
i$_2$—or a group

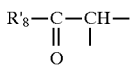

in which R'$_8$ is as defined above; i$_3$—or a group

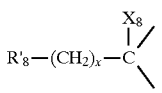

in which:
R'$_8$ is as defined above;
x is zero or one;
X$_8$ is a hydrogen; a hydroxyl; a C$_1$–C$_4$-alkoxy; an alkylcarbonyloxy in which the alkyl is C$_1$–C$_6$; a benzoyloxy; a carboxyl; an alkoxycarbonyl in which the alkoxy is C$_1$–C$_4$; an amino; a group —NR'$_3$COR'$_4$; a cyano; a group —CH$_2$NH$_2$; a group —CH$_2$NR'$_3$COR'$_4$; a group —CH$_2$OH; a group —CH$_2$—O-Alk in which Alk is a C$_1$–C$_4$-alkyl; or a group —CH$_2$—O—COR$_4$;
or X$_8$ forms an additional bond with the carbon atom to which it is bonded and with the adjacent carbon atom of the piperidine;
R'$_3$ is a hydrogen or a C$_1$–C$_4$-alkyl; and
R'$_4$ is a C$_1$–C$_7$-alkyl; a C$_3$–C$_7$-cycloalkyl which is unsubstituted or substituted by one or more methyls; a phenyl; or a pyridyl;
i$_4$—or a group

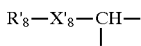

in which:
R'$_8$ is as defined above,
X'$_8$ is an oxygen atom; a sulfur atom; a sulfoxide; a sulfone; a group —NR'$_3$-; a group

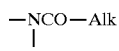

in which Alk is a C$_1$–C$_4$-alkyl; or a group

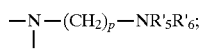

R'$_3$ is as defined above;

p is one, two or three; and

R′$_5$ and R′$_6$ are each independently a hydrogen or a C$_1$–C$_4$-alkyl;

or R′$_5$ and R′$_6$, together with the nitrogen atom to which they are bonded, form a heterocycle selected from pyrrolidine, piperidine and morpholine;

ii—or a group Am′$_2$ of the formula

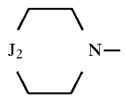

in which J$_2$ is:

ii$_1$—either a group

ii$_2$—or a group

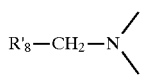

in which R′$_8$ is as defined above;

iii—or a group Am$_3$ of the formula

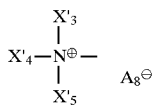

in which X′$_3$, X′$_4$ and X′$_5$ form, together with the nitrogen atom to which they are bonded, an azabicyclic or azatricyclic system containing from 5 to 9 carbon atoms which is unsubstituted or substituted by a phenyl or a benzyl;

A$_8^\ominus$ is an anion;

Ar$_8$ is a phenyl which is unsubstituted or monosubstituted or polysubstituted by a substituent selected from a halogen atom, a hydroxyl, a C$_1$–C$_4$-alkoxy, a C$_1$–C$_4$-alkyl and a trifluoromethyl, said substituents being identical or different; a thienyl; a benzothienyl; a naphthyl; or an indolyl which is unsubstituted or N-substituted by a C$_1$–C$_4$-alkyl or a benzyl;

R$_8$ is an ω-(C$_1$–C$_4$)alkoxy(C$_2$–C$_4$)alkylene; an ω(C$_1$–C$_4$) alkylcarbonyloxy(C$_2$–C$_4$)alkylene; an ω-benzoyloxy(C$_2$–C$_4$)alkylene; an ω-hydroxy(C$_2$–C$_4$)alkylene; an ω-(C$_1$–C$_4$)alkylthio(C$_2$–C$_4$)alkylene; an ω-(C$_1$–C$_4$)alkylcarbonyl(C$_2$–C$_4$) alkylene; an ω-carboxy(C$_2$–C$_4$)alkylene; or an ω-(C$_1$–C$_4$)alkoxycarbonyl(C$_2$–C$_4$)alkylene;

T$_8$ is a direct bond; a hydroxymethylene group; an alkoxymethylene group in which the alkoxy is C$_1$–C$_4$; a C$_1$–C$_5$-alkylene group; a vinylene; an oxygen atom; or a group -NR′$_7$-;

R′$_7$ is a hydrogen or a C$_1$–C$_4$-alkyl; and

Z$_8$ is:

a phenyl which is unsubstituted or monosubstituted or polysubstituted by a substituent selected from a halogen atom; a trifluoromethyl; a cyano; a hydroxyl; a nitro; an amino which is unsubstituted or monosubstituted or disubstituted by a C$_1$–C$_4$-alkyl; a benzylamino; a carboxyl; a C$_1$–C$_{10}$-alkyl; a C$_3$–C$_8$-cycloalkyl which is unsubstituted or monosubstituted or polysubstituted by a methyl; a C$_1$–C$_{10}$-alkoxy; a C$_3$–C$_8$-cycloalkoxy which is unsubstituted or monosubstituted or polysubstituted by a methyl; a mercapto; a C$_1$–C$_{10}$-alkylthio; an alkylcarbonyloxy in which the alkyl is C$_1$–C$_6$; an alkylcarbonylamino in which the alkyl is C$_1$–C$_6$; a benzoylamino; an alkoxycarbonyl in which the alkoxy is C$_1$–C$_4$; a cycloalkoxycarbonyl in which the cycloalkyl is C$_3$–C$_7$; a carbamoyl which is unsubstituted or monosubstituted or disubstituted by a C$_1$–C$_4$alkyl; an ureido which is unsubstituted or monosubstituted in the 3-position by a C$_1$–C$_4$-alkyl or a C$_3$–C$_7$-cycloalkyl; and a (1-pyrrolidino)carbonylamino, said substituents being identical or different;

a naphthyl which is unsubstituted or monosubstituted or polysubstituted by a halogen, a trifluoromethyl, a C$_1$–C$_4$-alkyl, a hydroxyl or a C$_1$–C$_4$-alkoxy; or a pyridyl; a thienyl; an indolyl; a quinolyl; a benzothienyl; or an imidazolyl;

with the limitation that R$_8$ cannot be an ω-(C$_1$–C$_4$) alkoxy(C$_2$–C$_4$)alkylene or an ω-(C$_1$–C$_4$)alkylcarbonyloxy(C$_2$–C$_4$)alkylene when Am$_8$ is a group Am$_3$;

and their possible salts with mineral or organic acids or their possible quaternary ammonium salts.

The compounds of formula VIII above can be obtained by the process which is characterized in that:

1) a compound of the formula

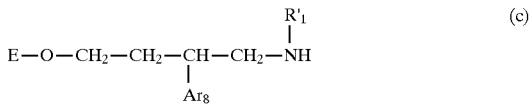

in which Ar$_8$ is as defined above, R′$_1$ is an ω-(C$_1$–C$_4$) alkoxy(C$_2$–C$_4$)alkylene, an ω-hydroxy(C$_2$–C$_4$) alkylene, an ω-(C$_1$–C$_4$)alkylthio(C$_2$–C$_4$)alkylene, an ω-(C$_1$–C$_4$)alkyl-carbonyl(C$_2$–C$_4$)alkylene, an ω-carboxy(C$_2$–C$_4$)alkylene or an ω-(C$_1$–C$_4$)alkoxycarbonyl(C$_2$–C$_4$)alkylene, it being understood that when R′$_1$ is an ω-hydroxy(C$_2$–C$_4$)alkylene, the hydroxyl can be protected, and E is hydrogen or an O-protecting group such as, for example, tetrahydropyran-2-yl, is treated either with a functional derivative of an acid of the formula

in which Z$_8$ is as defined above and T′$_8$ is a direct bond, a hydroxymethylene group, an alkoxymethylene group in which the alkoxy is C$_1$–C$_4$, a C$_1$–C$_5$-alkylene group or a vinylene, if it is intended to prepare a compound of formula (VIII) in which T$_8$ is a direct bond, a hydroxymethylene group, an alkoxymethylene group in which the alkoxy is C$_1$–C$_4$, a C$_1$–C$_5$-alkylene group or a vinylene, or with a chloroformate of the formula

in which Z$_8$ is as defined above, if it is desired to prepare a compound formula (VIII) in which T$_8$ is an oxygen, or with an isocyanate of the formula $$O=C=N-Z_8 \quad (f)$$

in which $Z_8$ is as defined above, if it is desired to prepare a compound of formula (VIII) in which $T_8$ is a group $-NR'_7-$ in which $R'_7$ is a hydrogen,
or with a carbamoyl chloride of the formula $$\underset{ClCON-Z_a}{\overset{R''_7}{|}} \quad (g)$$

in which $Z_8$ is as defined above and $R''_7$ is a $C_1-C_4$-alkyl, if it is desired to prepare a compound of formula (VIII) in which $T_8$ is a group $-NR'_7-$ in which $R'_7$ is a $C_1-C_4$-alkyl, to give a compound of the formula $$E-O-CH_2-CH_2-\underset{\underset{Ar_8}{|}}{CH}-CH_2-\underset{\underset{}{|}}{N}-CO-T_8-Z_8 \quad (h)$$
with $R'_1$ above N 2) if appropriate, when $R'_1$ is an $\omega$-hydroxy($C_2-C_4$) alkylene, an O-acylation reaction is performed to give a compound of the formula $$E-O-CH_2-CH_2-\underset{\underset{Ar_8}{|}}{CH}-CH_2-\underset{\underset{}{|}}{N}-CO-T_8-Z_8 \quad (h\ bis)$$
with $R''_1$ above N in which E, $Ar_8$, $T_8$ and $Z_8$ are as defined above and $R''_1$ is an $\omega$-($C_1-C_4$)alkyl-carbonyloxy($C_2-C_4$)alkylene or an $\omega$-benzoyloxy($C_2-C_4$)alkylene, or the hydroxyl is protected;

3) the compound obtained in step 1) or step 2) is then hydrolyzed to give the alcohol of the formula $$HO-CH_2-CH_2-\underset{\underset{Ar_8}{|}}{CH}-CH_2-\underset{\underset{}{|}}{N}-CO-T-Z \quad (i)$$
with $R_8$ above N 4) the alcohol (i) is treated with methanesulfonyl chloride to give the mesylate of the formula $$CH_3-SO_2-O-CH_2-CH_2-\underset{\underset{Ar_8}{|}}{CH}-CH_2-\underset{\underset{}{|}}{N}-CO-T_8-Z_8 \quad (j)$$
with $R_8$ above N 5) the mesylate (j) is reacted
either with a cyclic secondary amine of the formula

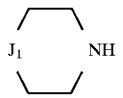 (k)

in which $J_1$ is as defined above, it being understood that when $J_1$ is the group

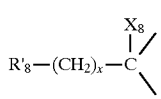

where $X_8$ is a hydroxyl or an amino, these groups can be protected;

or with a cyclic secondary amine of the formula

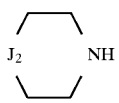 (l)

in which $J_2$ is as defined above,
or with a cyclic tertiary amine of the formula

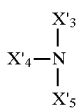 (m)

in which $X'_3$, $X'_4$ and $X'_5$ are as defined above, and 6) either, when a secondary amine of formula (k) or (l) is used and after optional deprotection of the hydroxyl groups or the amino group, the resulting product is optionally converted to one of its salts with a mineral or organic acid or one of its quaternary ammonium salts, or, when a tertiary amine of formula (m) is used and after optional deprotection of the hydroxyl group, the resulting product is isolated or the methanesulfonate anion of the resulting quaternary salt is optionally exchanged with another anion, for example a pharmaceutically acceptable anion.

The compounds according to patent application FR94 03701 are the compounds of formula IX:

$$B-(CH_2)_m-O-\underset{\underset{Ar_9}{|}}{\overset{R'_9}{\underset{|}{C}}}-CH_2-\underset{\underset{}{|}}{\overset{R''_9}{N}}-T_9-A_9-Z_9 \quad (IX)$$

in which:

B is:
either the group $B_1$ of the formula

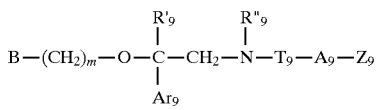

in which p=1 or 2, $R_3$ is hydrogen, a $C_1-C_4$-alkyl or the phenyl group and $X^-$ is an anion,
or the group $B_2$ of the formula

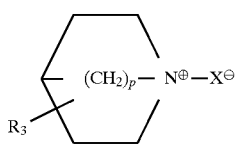

in which:
Ar' is an unsubstituted phenyl group; a phenyl group monosubstituted or polysubstituted by a halogen, a nitro group, a hydroxyl group, a trifluoromethyl group, a $C_1-C_4$-alkyl group or a $C_1-C_4$-alkoxy group; or a pyridyl group; and Y' is a hydroxyl group, an amino group or one of the following groups:

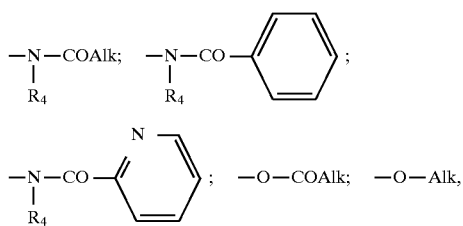

in which:
R$_4$ is hydrogen or a C$_1$–C$_4$-alkyl group; and
Alk is a C$_1$–C$_7$-alkyl group;
m is equal to 2 or 3;
R'$_9$ is hydrogen or a C$_1$–C$_4$-alkyl group;
R"$_9$ is a hydrogen; a C$_1$–C$_4$-alkyl; an ω-(C$_1$–C$_4$) alkoxy(C$_2$–C$_4$)alkylene; an ω-(C$_1$–C$_4$) alkylcarbonyloxy(C$_2$–C$_4$)alkylene; an ω-hydroxy(C$_2$–C$_4$)alkylene; an ω-(C$_1$–C$_4$) alkylthio(C$_2$–C$_4$)alkylene; an ω-(C$_1$–C$_4$) alkoxycarbonyl(C$_2$-C$_4$)alkylene; an ω-carboxy (C$_2$–C$_4$)alkylene; an ω-(C$_1$–C$_4$)alkylcarbonyl (C$_2$–C$_4$)alkylene; or an ω-benzoyloxy(C$_2$–C$_4$) alkylene;
or R'$_9$ and R"$_9$ together form a group —(CH$_2$)$_n$—CQ—, where Q=H$_2$ or O and n is equal to 1, 2 or 3;
T$_9$ is the group —CH$_2$— or one of the groups

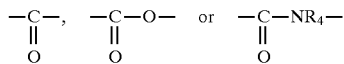

in which R$_4$ is hydrogen or a (C$_1$–C$_4$)alkyl group, with the proviso that T$_9$ is —CH$_2$— when Q is oxygen and one of the following groups:

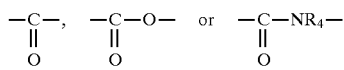

when Q is hydrogen;
A$_9$ is a direct bond, a group —(CH$_2$)$_t$—, in which t is equal to 1, 2 or 3, or a group —CH═CH—;
Z$_9$ is an unsubstituted phenyl; a phenyl monosubstituted or polysubstituted by a halogen, a hydroxyl group, a nitro group, a (C$_1$–C$_4$)alkyl group, a trifluoromethyl group or a (C$_1$–C$_4$) alkoxy group; a 1-naphthyl group; or a 2-naphthyl group; and
Ar$_9$ is an unsubstituted phenyl group, a phenyl group monosubstituted or polysubstituted by a substituent selected from a halogen atom, a trifluoromethyl, a hydroxyl, a C$_1$–C$_4$-alkoxy and a C$_1$–C$_4$-alkyl, said substituents being identical or different; a thienyl; a benzothienyl; a naphthyl; or an indolyl optionally N-substituted by a C$_1$–C$_4$-alkyl or a benzyl; and their possible salts with mineral or organic acids.

The compounds of formula IX above can be obtained by process A or process B below.

Process A is suitable for obtaining the compounds of formula IX in which R'$_9$ and R"$_9$ together form a group —(CH$_2$)$_n$—CQ in which Q is oxygen.

This process consists in:
1) treating a compound of formula (II):

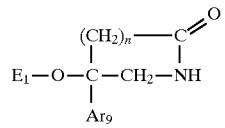

in which Ar$_9$, R'$_9$ and R"$_9$ are as defined above and E$_1$ is an O-protecting group, in particular the tetrahydropyran-2-yl group, with a halogenated derivative of the formula
in which Hal is a halogen atom, preferably bromine, and A$_9$ and Z$_9$ are as defined above, in the presence of a base such as, for example, sodium hydride or potassium tert-butoxide, to form the compound of the formula

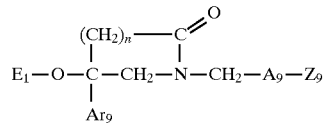

2) removing the protecting group E$_1$ by reaction with an acid;
3) treating the resulting compound of formula (d1):

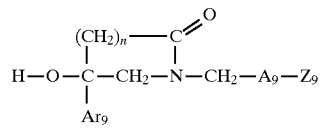

with a compound of formula (e1):

in which E$_2$ is an O-protecting group such as the tetrahydropyran-2-yl group, to form the compound of formula (f1):

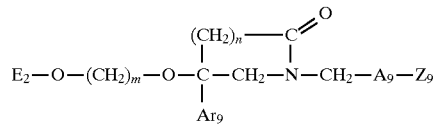

in which E$_2$, m, Ar$_9$, R'$_9$, R"$_9$, T$_9$, A$_9$ and Z$_9$ are as defined above;
4) removing the protecting group E$_2$ by reaction with an acid;
5) treating the resulting compound of formula (g1):

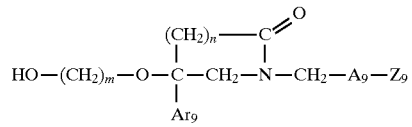

with methanesulfonyl chloride;
6) reacting the resulting mesylate of the formula

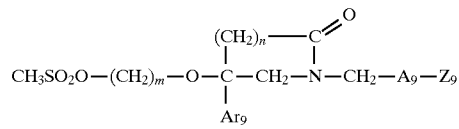

either with a cyclic secondary amine of formula (Xa):

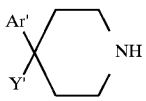

in which Ar' and Y' are as defined above, it being understood that when Y' is a hydroxyl or an amino, these groups can be protected;
or with a cyclic tertiary amine of formula (Xb):

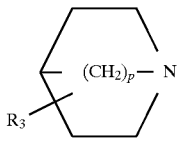

in which p and $R_3$ are as defined above; and
7)—either, when using a cyclic secondary amine of formula (Xa) and after optional deprotection of the hydroxyl or amino groups, optionally converting the product obtained in step 6) to one of its salts with a mineral or organic acid;
or, when using a cyclic tertiary amine of formula (Xb), isolating the product obtained in step 6) or optionally exchanging the methanesulfonate anion of the resulting quaternary salt with another, pharmaceutically acceptable anion.

Process B is suitable for obtaining the compounds of formula IX in which
$R'_9$ and $R''_9$ together form a group $-(CH_2)_n-CQ-$ where $Q=H_2$ and n=1, 2 or 3, or $R'_9$ and $R''_9$ are different and are as defined above.

This process B consists in:
1) removing the O-protecting group $E_1$ from a compound of the formula

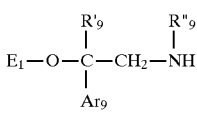

in which $R'_9$ and $Ar_9$ are as defined above, $R'_9$ is a hydrogen, a $C_1-C_4$-alkyl, an $\omega$-($C_1-C_4$)alkoxy($C_2-C_4$)alkylene, an $\omega$-hydroxy($C_2-C_4$)alkylene, an $\omega$-($C_1-C_4$)alkyl-thio($C_2-C_4$)alkylene, an $\omega$-($C_1-C_4$)alkoxycarbonyl($C_2-C_4$)alkylene, an $\omega$-carboxy($C_2-C_4$)alkylene or an $\omega$-carboxy($C_2-C_4$)alkylene or an $\omega$-($C_1-C_4$)alkylcarbonyl($C_2-C_4$)alkylene, or $R'_9$ and $R''_9$ together form a group $-(CH_2)_n-CQ-$ (n=1, 2 or 3 and $Q=H_2$), and $E_1$ is an O-protecting group, in particular the tetrahydropyran-2-yl group, by reaction with an acid;
2) protecting the amine group of the resulting compound of the formula

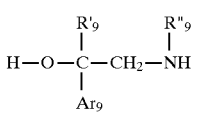

by reaction with di-tert-butyl dicarbonate ($Boc_2O$), for example, in a solvent such as dioxane, to give the compound of the formula

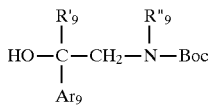

3) optionally, when $R''_9$ in the compound of formula (a2) is an $\omega$-hydroxy($C_2-C_4$)alkylene, protecting the amine group as indicated in step 2) and then protecting the hydroxyl, or performing an O-acylation reaction, to give a compound of the formula

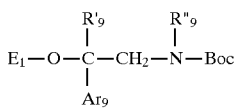

in which $E_1$, $R'_9$ and $Ar_9$ are as defined above and $R''_9$ is an $\omega$-($C_1-C_4$)alkyl-carbonyloxy($C_2-C_4$)alkylene or an $\omega$-benzoyloxy($C_2-C_4$)alkylene, and then selectively removing the protecting group $E_1$ by acid hydrolysis to give the compound of the formula

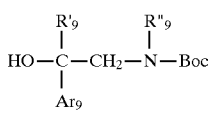

4) treating the compound (c2) or (c'2) obtained in step 2) or step 3), it being understood that when $R''_9$ is an $\omega$-hydroxy($C_2-C_4$)alkylene, the hydroxyl is protected, with a compound of formula (d1):

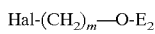

in which $E_2$ is an O-protecting group such as the tetrahydropyran-2-yl group, to form the compound of the formula

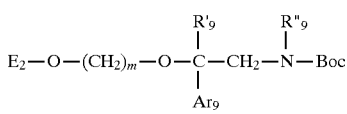

in which $E_2$, m, $Ar_9$, $R'_9$ and $R''_9$ are as defined above;
5) selectively removing the protecting group $E_2$, for example by reaction with pyridinium paratoluenesulfonate when $E_2$ is a tetrahydropyran-2-yl, to give a compound of the formula

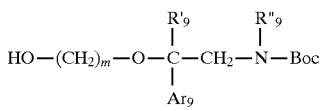

6) treating the compound (f2), it being understood that when $R''_9$ is an $\omega$-hydroxy($C_2-C_4$)alkylene, the hydroxyl is protected, with methanesulfonyl chloride to give the mesylate of the formula

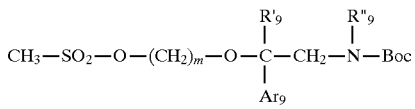

7) reacting the mesylate (g2)

either with a cyclic secondary amine of the formula

 (Xa)

in which Ar' and Y' are as defined above, it being understood that when Y' is a hydroxyl or an amino, these groups can be protected.

or with a cyclic tertiary amine of the formula

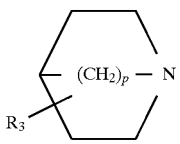 (Xb)

in which p and $R_3$ are as defined above, to give the compound of the formula

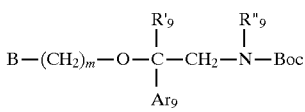 (h2)

8) deprotecting the N-protecting group of the compound (h2) by treatment in a strong acid medium, for example HCl, to give the compound of the formula

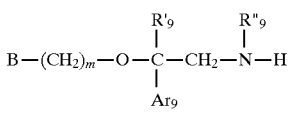 (i2)

9) reacting the compound of formula (i2)
either with a halogenated derivative of the formula

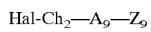 (j)

in which Hal is a halogen atom, preferably bromine, and $A_9$ and $Z_9$ are as defined above, when $R'_9$ and $R''_9$ are different and if it is desired to prepare a compound of formula (IX) in which $T_9$ is —$CH_2$—, or with a functional derivative of an acid of the formula HO—CO—$A_9$—$Z_9$ (ja)

in which $A_9$ and $Z_9$ are as defined above, if it is desired to prepare a compound of formula (IX) in which $T_9$ is —CO—;

or with a chloroformate of the formula

Cl—COO—$A_9$—$Z_9$ (jb)

in which $A_9$ and $Z_9$ are as defined above, if it is desired to prepare a compound of formula (IX) in which $T_9$ is —COO—, or with an isocyanate of the formula O=C=N—$A_9$—$Z_9$ (jc)

in which $A_9$ and $Z_9$ are as defined above, if it is desired to prepare a compound of formula (IX) in which $T_9$ is —CO—NH—, or with a carbamoyl chloride of the formula

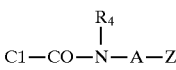 (jd)

in which A and Z are as defined above and $R_4$ is a ($C_1$–$C_4$)alkyl group, if it is desired to prepare a compound of formula (IX) in which $T_9$ is —CO—$NR_4$— in which $R_4$ is a ($C_1$–$C_4$)alkyl; and 10)—either, when using a cyclic secondary amine of formula (Xa) in step 7) and after optional deprotection of the hydroxyl or amino groups, optionally converting the product obtained in step 9) to one of its salts with a mineral or organic acid;

or, when using a cyclic tertiary amine of formula (Xb) in step 7), isolating the product obtained in step 9) or optionally exchanging the anion of the resulting quaternary salt with another, pharmaceutically acceptable anion The spirolactam derivatives of general formula (Xa) or (Xb) and their solvation products or their acid addition salts described in patent application EP-A1-0 360 390 are also $NK_1$ receptor antagonists which are appropriate for the purposes of the invention:

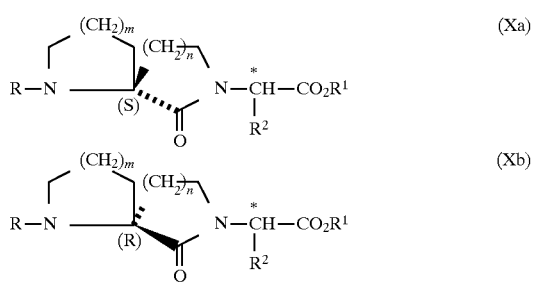

in which:
R is a hydrogen atom or a conventional nitrogen-protecting group;
$R^1$ is a hydrogen atom or a conventional protecting group or activating group for the carboxyl group;
$R^2$ is the side chain of a natural amino acid;
m is 1 or 2; and
n is 1 or 2;
it being possible for the configuration at * to be (R) or (S) or a mixture thereof, with the proviso that when R is the nitrogen-protecting group $R^3$—CO(O)— (in which $R^3$ is ($CH_3$)$_3$C—), the group —$CO_2R^1$ is the protected carboxyl group —$CO_2CH_3$, m is 1 and n is 1 in the compounds of formula (Ib), $R^2$ cannot be an arylmethyl group.

The isoindolone derivatives of formula XI described in patent application EP-A1-429 366 are also $NK_1$ receptor antagonists which are appropriate for the purposes of the invention:

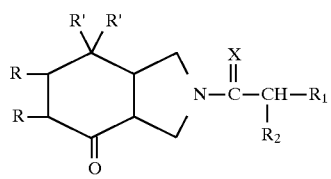 XI in which:
the radicals R are identical and are hydrogen atoms or together form a bond;

the radicals R' are identical and are phenyl radicals optionally substituted by a halogen atom or by a methyl radical in the 2- or 3-position;

X is an oxygen or sulfur atom or a radical N-$R_3$, in which $R_3$ is a hydrogen atom or a $C_1$–$C_{12}$-alkyl radical optionally substituted by one or more carboxyl, dialkylamino, acylamino, alkoxycarbonyl, alkoxycarbonylamino, carbamoyl, alkylcarbamoyl or dialkylcarbamoyl radicals (it being possible for the alkyl moieties of these radicals to themselves carry a dialkylamino or phenyl substituent) or substituted by phenyl radicals, phenyl radicals substituted (by a halogen, an alkyl, an alkoxy or a dialkylamino), or naphthyl, thienyl, furyl, pyridyl or imidazolyl radicals, or $R_3$ is a dialkylamino radical;

$R_1$ is a phenyl radical optionally substituted by one or more halogen atoms or by hydroxyl radicals; an alkyl radical optionally substituted (by halogen atoms or amino, alkylamino or dialkylamino radicals); an alkoxy or alkylthio radical optionally substituted (by hydroxyl radicals or dialkylamino radicals, the alkyl moieties of which can form, with the nitrogen atom to which they are attached, a 5- or 6-membered heterocycle which may contain another heteroatom selected from oxygen, sulfur and nitrogen optionally substituted by an alkyl radical), or substituted by amino, alkylamino or dialkylamino radicals, the alkyl moieties of which can form, with the nitrogen atom to which they are bonded, a heterocycle as defined above, or is a cyclohexadienyl or naphthyl radical or a saturated or unsaturated, monocyclic or polycyclic heterocyclyl radical containing 5 to 9 carbon atoms and one or more heteroatoms selected from oxygen, nitrogen and sulfur; and $R_2$ is a hydrogen or halogen atom or a hydroxyl, alkyl, aminoalkyl, alkylamino-alkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxy-carbonylamino radical, the above-mentioned alkyl and acyl radicals being linear or branched and containing 1 to 4 carbon atoms.

The compounds of formula XII below and their pharmaceutically acceptable salts described in patent application EP-A2-0 436 334 are also $NK_1$ receptor antagonists which are suitable for the purposes of the invention:

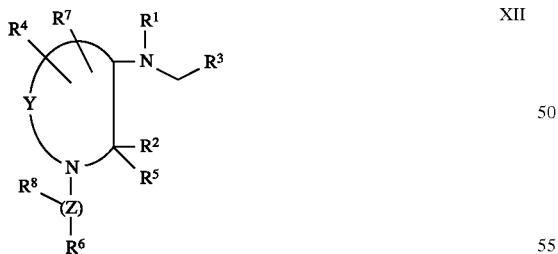

in which:

Y is the group $(CH_2)_n$, in which n is an integer from 1 to 4, in which one of the single carbon-carbon bonds of said $(CH_2)_n$ can optionally be replaced with a carbon-carbon double bond, in which one of the carbon atoms of said $(CH_2)_n$ can optionally be substituted by $R^4$, and in which one of the carbon atoms of said $(CH_2)_n$ can optionally be substituted by $R^7$;

Z is $(CH_2)_m$, in which m is an integer from 0 to 6, in which one of the carbon-carbon single bonds of said $(CH_2)_m$ can optionally be replaced with a carbon-carbon double bond or a carbon-carbon triple bond, and in which one of the carbon atoms of said $(CH_2)_m$ can optionally be substituted by $R^8$, $R^1$ is hydrogen or a $C_1$–$C_4$-alkyl optionally substituted by a hydroxyl, a $C_1$–$C_4$-alkoxy or fluorine;

$R^2$ is a radical selected from hydrogen; a linear or branched $C_1$–$C_6$-alkyl group; a $C_3$–$C_7$-cycloalkyl group in which one of the $CH_2$ groups of said cycloalkyl can optionally be replaced with NH, oxygen or sulfur; an aryl group selected from phenyl and naphthyl groups; a heteroaryl group selected from indanyl, thienyl, furyl, pyridyl, thiazolyl, isothiazolyl, oxazolyl, isoxazolyl, triazolyl, tetrazolyl and quinolyl groups; and phenyl($C_2$–$C_6$)alkyl, benzhydryl and benzyl groups; in said radical $R_2$, each of said aryl and heteroaryl groups, and the phenyl moieties of said benzyl, phenyl($C_2$–$C_6$)alkyl and benzhydryl, can optionally be substituted by one or more substituents independently selected from halogeno, nitro, $C_1$–$C_6$-alkyl, $C_1$–$C_6$-alkoxy, trifluoromethyl, amino and $(C_1$–$C_6)$alkylamino groups and the following groups:

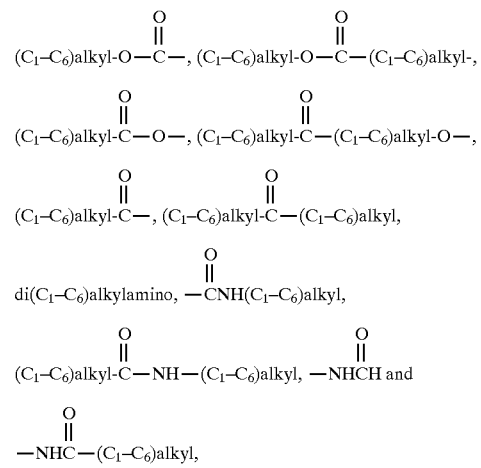

and each of the phenyl moieties of said benzhydryl can optionally be replaced with a naphthyl, a thienyl, a furyl or a pyridyl;

$R^5$ is hydrogen, a phenyl or a $C_1$–$C_6$-alkyl;

or $R^2$ and $R^5$, with the carbon atom to which they are bonded, form a saturated ring having from 3 to 7 carbon atoms in which one of the $CH_2$ groups of said ring can optionally be replaced with oxygen, NH or sulfur;

$R^3$ is an aryl selected from phenyl and naphthyl groups, a heteroaryl selected from indanyl, thienyl, furyl, pyridyl, thiazolyl, isothiazolyl, oxazolyl, isoxazolyl, triazolyl, tetrazolyl and quinolyl groups; or a $C_3$–$C_7$-cycloalkyl in which one of the $CH_2$ groups can optionally be replaced with NH, oxygen or sulfur; in said group $R^3$, each of said aryl and heteroaryl groups can optionally be substituted by one or more substituents and said $C_3$–$C_7$-cycloalkyl can optionally be substituted by one or two substituents, each of said substituents being independently selected from halogeno, nitro, $C_1$–$C_6$-alkyl, $C_1$–$C_6$-alkoxy, methyl, trifluoromethyl, amino and $(C_1$–$C_6)$alkylamino groups and the following groups:

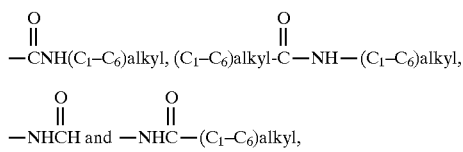

$R^4$ and $R^7$ are each independently selected from hydrogen, hydroxyl, halogeno, amino, oxo, cyano, methyl, hydroxymethyl, halogenomethyl, ($C_1$–$C_6$) alkylamino, di($C_1$–$C_6$)alkylamino and ($C_1$–$C_6$)alkoxy groups, the following groups:

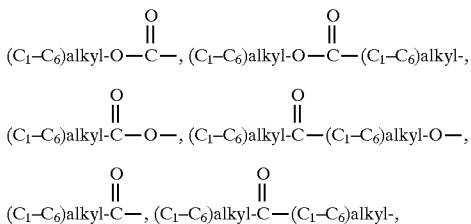

and the radicals indicated in the definition of $R^2$;

$R^6$ is the group $NHCOR_9$ $NHCH_2R^9$ or $SO_2R^9$ or one of the radicals indicated in any one of the definitions of $R^2$, $R^4$ and $R^7$;

$R^8$ is an oximido (=NOH) or one of the radicals indicated in any one of the definitions of $R^2$, $R^4$ and $R^7$; and $R^9$ is hydrogen, a $C_1$–$C_6$-alkyl, a phenyl or a phenyl ($C_1$–$C_6$)alkyl, with the proviso that (a) when m is O, $R^8$ is absent, (b) when $R^4$, $R^6$, $R^7$ or $R^8$ is as defined in $R^2$, it cannot form a ring with the carbon atom to which it is bonded and with $R^5$, and (c) when $R^4$ and $R^7$ are bonded to the same carbon atom, then either each radical $R^4$ and $R^7$ is independently selected from hydrogen, fluorine and a $C_1$–$C_6$)-alkyl, or $R^4$ and $R^7$, with the carbon atom to which they are bonded, form a saturated $C_1$–$C_6$ carbocyclic ring which forms a spiro compound with the nitrogen-containing ring to which they are bonded.

The compounds of formula XIII below, their salts or their prodrugs described in patent application EP-A1-0 499 313 are also $NK_1$ receptor antagonists which are useful according to the present invention:

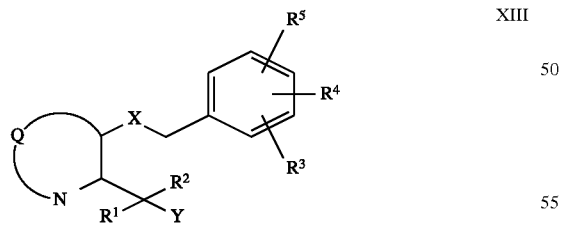

in which:

Q is the radical of a system such as an optionally substituted azabicycli c ring;

X is an oxa or a thia;

Y is hydrogen or a hydroxyl;

$R^1$ and $R^2$ independently are a phenyl or thienyl group, each one optionally being substituted by a halogeno or a trifluoromethyl;

$R^3$, $R^4$ and $R^5$ independently are hydrogen, a $C_1$–$C_6$-alkyl, a $C_2$–$C_6$-alkenyl, a $C_2$–$C_6$-alkynyl, a halogeno, a cyano, a nitro, a trifluoromethyl, a trimethylsilyl, —$OR^a$, $SCH_3$, $SOCH_3$, $SO_2CH_3$, —$NR^aR^b$, —$NR^aCOR^b$, —$NR^aCO_2R^b$, —$CO_2R^a$ or —$CONR^aR^b$; and $R^a$ and $R^b$ independently are hydrogen, a $C_1$–$C_6$-alkyl, a phenyl or a trifluoromethyl.

The compounds of formula XIV described in patent application EP-A2-0 585 913 are also $NK_1$ receptor antagonists which are useful according to the present invention:

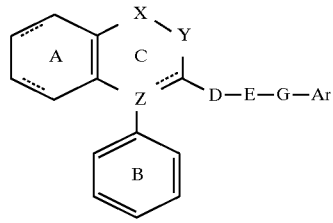

in which:

the ring A can be substituted;

the ring B is an optionally substituted benzene ring;

either X or Y is —$NR^1$— ($R^1$ is a hydrogen atom, an optionally substituted hydro-carbon group, an optionally substituted hydroxyl group or an optionally substituted amino group), —O— or —S—, the other being —CO—, —CS— or —C($R^2$)$R^{2a}$— ($R^2$ and $R^{2a}$ independently are a hydrogen atom or an optionally substituted hydrocarbon group), or X or Y is —N=, the other being =$CR^3$— ($R^3$ is a hydrogen atom, a halogen atom, an optionally substituted hydrocarbon group, an optionally substituted amino group, a substituted hydroxyl group or a mercapto group substituted by an optionally substituted hydrocarbon group);

... is a single bond or a double bond; (i) when ... adjacent to Z is a single bond, Z is —$CR^4$– ($R^4$ is a hydrogen atom, a hydroxyl group or an optionally substituted hydrocarbon group) or a nitrogen atom, or (ii) when ... adjacent to Z is a double bond, Z is a carbon atom;

D is a $C_1$–$C_3$-alkylene group which can be substituted by an oxo group or a thioxo group, or D and Y, taken together, can form a 5- to 7-membered ring which can be substituted by an oxo group or a thioxo group;

E is —$NR^5$— ($R^5$ is a hydrogen atom or an optionally substituted hydrocarbon group), —O— or —S(O)$_n$—(n is equal to 0, 1 or 2), or $R^5$ and Y, taken together, form a 5- to 7-membered ring which can be substituted by an oxo group or a thioxo group;

G is a bond or a $C_1$–$C_3$-alkylene group; and

Ar is an optionally substituted aryl group or an optionally substituted heterocyclic group, with the proviso that (1) when (i) —X—Y— is —O—CO— or —CO—O—, (ii) D is —CO— and (iii) E is —$NR^5$—, either (a) G is a $C_1$–$C_3$-alkylene group and Ar is a substituted aryl group or a substituted heterocyclic group, or (b) G is a bond and $R^5$ is an optionally substituted hydrocarbon group, and (2) when —X—Y— is —NH—CO—, D is —CO—.

The quinuclidine derivatives of formulae XVa, XVb and XVc and their pharmaceutically acceptable salts described in patent application WO90/05525 are also $NK_1$ receptor antagonists which are useful according to the present invention:

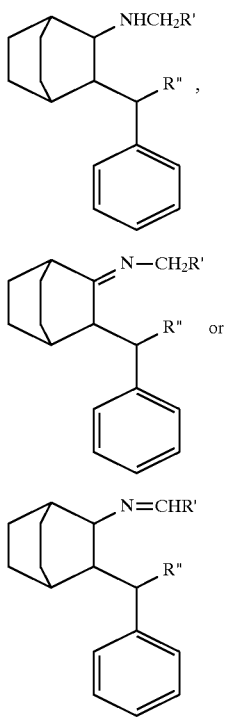

in which:

R' is a $C_5$–$C_7$-cycloalkyl, norbornyl, pyrrolyl, thienyl, pyridyl, indolyl, biphenyl or phenyl group optionally substituted by one or two substituents selected from fluoro, chloro, bromo, trifluoromethyl, $C_1$–$C_3$-alkyl, $C_1$–$C_3$-alkoxy, carboxyl, ($C_1$–$C_3$)-alkoxycarbonyl and benzyloxycarbonyl groups, and R" is a branched $C_3$–$C_4$-alkyl, a branched $C_5$–$C_6$-alkenyl, a $C_5$–$C_7$-cycloalkyl, a furyl, a thienyl, a pyridyl, an indolyl, a biphenyl or a phenyl optionally substituted by one or two substituents selected from fluoro, chloro, bromo, trifluoromethyl, $C_1$–$C_3$-alkyl, $C_1$–$C_3$-alkoxy, carboxyl, ($C_1$–$C_3$)alkoxycarbonyl and benzyloxycarbonyl groups, with the proviso that R" is not an unsubstituted phenyl when R' is an unsubstituted phenyl, a pyrrolyl or a thienyl.

The quinuclidine derivatives of formulae XVIa, XVIb and XVIc and their pharmaceutically acceptable salts described in patent application WO90/05729 are also $NK_1$ receptor antagonists which are useful according to the present invention:

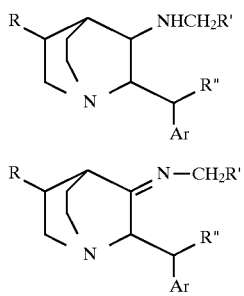

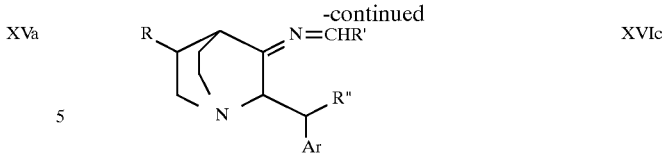

in which:

Ar is a thienyl, phenyl, fluorophenyl, chlorophenyl or bromophenyl group;

R is hydrogen or a $C_1$–$C_4$-alkyl;

R' is a $C_5$–$C_7$-cycloalkyl, norbornyl, pyrrolyl, 2,3-dihydrobenzofuranyl, thienyl, ($C_1$–$C_3$)alkoxy thienyl, pyridyl, hydroxypyridyl, quinolinyl, indolyl, naphthyl, ($C_1$–$C_3$)-alkoxynaphthyl, biphenyl, 2,3-methylenedioxyphenyl or phenyl group optionally substituted by one or two substituents selected from cyano, nitro, amino, N-mono($C_1$–$C_3$)alkylamino, fluoro, chloro, bromo, trifluoromethyl, $C_1$–$C_3$-alkyl, $C_1$–$C_3$-alkoxy, allyloxy, hydroxyl, carboxyl, ($C_1$–$C_3$) alkoxycarbonyl, benzyloxycarbonyl, carboxybenzyloxy, ($C_1$–$C_3$)alkoxycarbonylbenzyloxy, carboxamido and N,N-di($C_1$–$C_3$)alkylcarboxamido groups; and R" is a branched $C_3$–$C_4$-alkyl, branched $C_5$–$C_6$-alkenyl, $C_5$–$C_7$-cycloalkyl, furyl, thienyl, pyridyl, indolyl, biphenyl or phenyl group optionally substituted by one or two substituents selected from fluoro, chloro, bromo, trifluoromethyl, $C_1$–$C_3$-alkyl, phenyl($C_1$–$C_3$)alkyl, $C_1$–$C_3$-alkoxy, allyloxy, hydroxyl, carboxyl, ($C_1$–$C_3$) alkoxy-carbonyl and benzyloxycarbonyl groups, with the proviso that R" is never an unsubstituted phenyl, a fluorophenyl, a chlorophenyl, a bromophenyl or an alkyl-phenyl when R' is an unsubstituted phenyl, a pyrrolyl or a thienyl and Ar is other than a thienyl.

The compounds of formula XVII and their pharmaceutically acceptable salts described in patent application WO91/09844 are also $NK_1$ receptor antagonists which are useful according to the present invention:

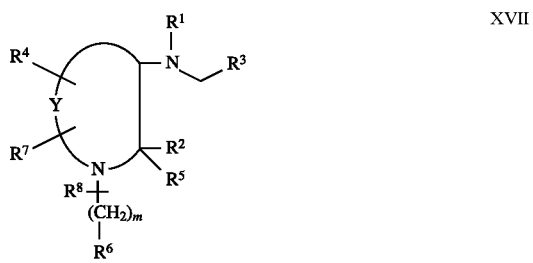

in which:

Y is $(CH_2)_n$, in which n is an integer from 2 to 4, in which one of the carbon-carbon single bonds of said $(CH_2)_n$ can optionally be replaced with a carbon-carbon double bond, in which one of the carbon atoms of said $(CH_2)_n$ can optionally be substituted by $R^4$, and in which any one of the carbon atoms of said $(CH_2)_n$ can optionally be substituted by $R^7$;

m is an integer from 0 to 6, one of the carbon-carbon single bonds of said $(CH_2)_m$ can optionally be replaced with a carbon-carbon double bond, and one of the carbon atoms of said $(CH_2)_m$ can optionally be substituted by $R^8$;

$R^1$ is a $C_1$–$C_6$-alkyl or hydrogen;

$R^2$ is a radical selected from hydrogen; a linear or branched $C_1$–$C_6$-alkyl group; a $C_3$–$C_7$-cycloalkyl group in which one of the carbon atoms can optionally be replaced with nitrogen, oxygen or sulfur; an aryl group selected from phenyl and naphthyl groups; a heteroaryl group selected from indanyl, thienyl, furyl, pyridyl and quinolyl groups; and phenyl($C_2$–$C_6$)alkyl, benzhydryl and benzyl groups; in said radical $R^2$, each of said aryl and heteroaryl groups, and the phenyl moieties of said benzyl, phenyl($C_2$–$C_6$)alkyl and benzhydryl, can optionally be substituted by one or more substituents independently selected from halogeno, nitro, $C_1$–$C_6$-alkyl, $C_1$–$C_6$-alkoxy, trifluoromethyl, amino and ($C_1$–$C_6$)alkylamino groups and the following groups:

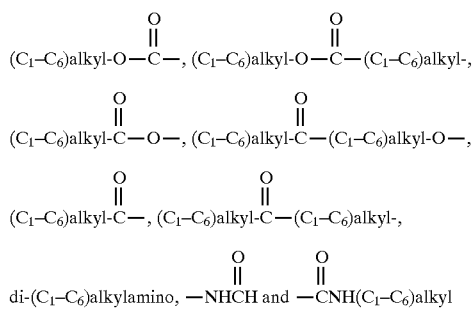

$R^5$ is hydrogen;

or $R^2$ and $R^5$, with the carbon atom to which they are bonded, form a saturated $C_3$–$C_7$ carbocyclic ring in which one of said carbon atoms can optionally be replaced with oxygen, nitrogen or sulfur;

$R^3$ an aryl selected from phenyl and naphthyl groups; a heteroaryl selected from indanyl, thienyl, furyl, pyridyl and quinolyl groups; of a $C_3$–$C_7$-cycloalkyl in which one of said carbon atoms can optionally be replaced with nitrogen, oxygen or sulfur; in said group $R^3$, each of said aryl and heteroaryl groups can optionally be substituted by one or more substituents and said $C_3$–$C_7$-cycloalkyl can optionally be substituted by one or two substituents, said substituents being independently selected from halogeno, nitro, $C_1$–$C_6$-alkyl, $C_1$–$C_6$-alkoxy, trifluoromethyl, amino and ($C_1$–$C_6$)alkylamino groups and the following groups:

$R^4$, $R^6$, $R^7$ and $R^8$ are each independently selected from hydrogen, hydroxyl, halogeno, amino and ($C_1$–$C_6$) alkylamino groups, the following groups:

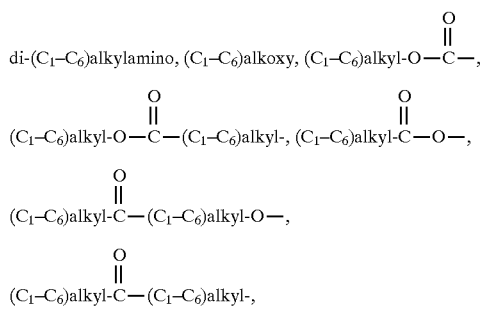

and the radicals previously indicated in the definition of $R^2$, with the proviso that (a) when m is 0, $R^8$ is absent, (b) neither $R^4$, nor $R^6$, nor $R^7$ can form a ring with the carbon atom to which it is bonded and with $R^5$, and (c) when $R^4$ and $R^7$ are bonded to the same carbon atom, then either each radical $R^4$ and $R^7$ is independently selected from hydrogen and a $C_1$–$C_6$-alkyl, or $R^4$ and $R^7$, with the carbon atom to which they are bonded, form a saturated $C_3$–$C_6$ carbocyclic ring which forms a spiro compound with the nitrogen-containing ring to which they are bonded.

The compounds of formula XVIII and their pharmaceutically acceptable salts described in patent application WO91/18899 are also $NK_1$ receptor antagonists which are useful according to the present invention:

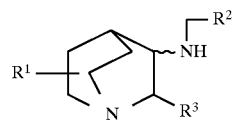

in which $R^1$ is hydrogen or a $C_1$–$C_6$-alkyl, $R^2$ is a phenyl, a pyridyl, a thienyl or a furyl, it being possible for $R^2$ optionally to be substituted by one to three substituents independently selected from $C_1$–$C_4$-alkyl, $C_1$–$C_4$-alkoxy, chloro, fluoro, bromo, iodo and trifluoromethyl groups, and $R^3$ is a phenyl, naphthyl, pyridyl, thienyl or furyl group, it being possible for $R^3$ optionally to be substituted by one to three substituents independently selected from $C_1$–$C_4$-alkyl, $C_1$–$C_4$-alkoxy, chloro, fluoro, bromo, iodo and trifluoromethyl groups.

The compounds of formulae XIXa, XIXb and XIXc and their pharmaceutically acceptable salts described in patent application WO92/01688 are also $NK_1$ receptor antagonists which are useful according to the present invention:

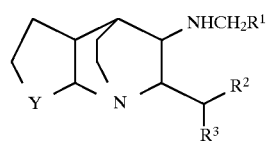

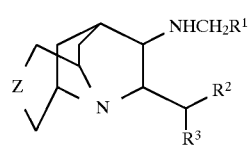

or

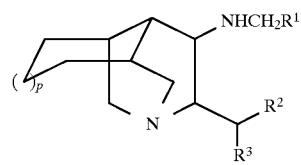

in which:

Y is the group $(CH_2)_m$, in which m is an integer from 1 to 3, or Y is a group of the formula

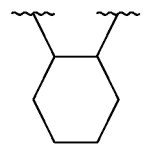

(J)

p is an integer from 0 to 1;

Z is oxygen, sulfur, an amino, an N—($C_1$–$C_3$)alkylamino or —$(CH_2)_n$— and n is equal to 0, 1 or 2;

$R^3$ is selected from thienyl, phenyl, fluorophenyl, chlorophenyl and bromophenyl groups;

$R^1$ is selected from $C_5$–$C_7$-cycloalkyl, pyrrolyl, thienyl, pyridyl and phenyl groups and phenyl groups substituted by one to three substituents selected from fluoro, chloro, bromo, trifluoromethyl, $C_1$–$C_3$-alkyl, $C_1$–$C_3$-alkoxy, carboxyl, ($C_1$–$C_3$)-alkoxycarbonyl and benzyloxycarbonyl groups, and $R^2$ is a furyl, thienyl, pyridyl, indolyl, biphenyl or phenyl group or a phenyl group substituted by one or two substituents selected from fluoro, chloro, bromo, trifluoromethyl, $C_1$–$C_3$-alkyl, $C_1$–$C_3$-alkoxy, carboxyl, ($C_1$–$C_3$)alkoxycarbonyl and benzyloxycarbonyl groups.

The compounds of formula XX and their pharmaceutically acceptable salts described in patent application WO92/06079 are also suitable for the purposes of the invention:

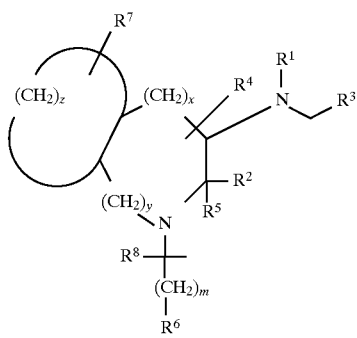

XX in which:

x is an integer from 0 to 4;

y is an integer from 0 to 4;

z is an integer from 1 to 6;

the ring containing $(CH_2)_z$ can contain from zero to three double bonds and one of the carbon atoms of $(CH_2)_z$ can optionally be replaced with oxygen, sulfur or nitrogen;

m is an integer from 0 to 12, one of the carbon-carbon single bonds of $(CH_2)_m$ can optionally be replaced with a carbon-carbon double or triple bond, and one of the carbon atoms of said $(CH_2)_m$ can optionally be substituted by $R^8$;

$R^1$ is hydrogen or a $C_1$–$C_6$-alkyl optionally substituted by a hydroxyl, an alkoxy or fluorine;

$R^2$ is a radical selected from hydrogen; a linear or branched $C_1$–$C_6$-alkyl group; a $C_3$–$C_7$-cycloalkyl group in which one of the carbon atoms can optionally be replaced with nitrogen, oxygen or sulfur; an aryl group selected from phenyl and naphthyl groups; a heteroaryl group selected from indanyl, thienyl, furyl, pyridyl, thiazolyl, isothiazolyl, oxazolyl, isoxazolyl, triazolyl, tetrazolyl and quinolyl groups; and phenyl ($C_2$14 $C_6$)alkyl, benzhydryl and benzyl groups, in said group $R^2$, each of said aryl and heteroaryl groups, and the phenyl moieties of said benzyl, phenyl($C_2$–$C_6$)alkyl and benzhydryl groups, can optionally be substituted by one or more substituents independently selected from halogeno, nitro, $C_1$–$C_6$-alkyl, $C_1$–$C_6$-alkoxy, trifluoromethyl and amino groups and the following groups:

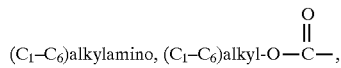

($C_1$–$C_6$)alkylamino, ($C_1$–$C_6$)alkyl-O—C—,

-continued

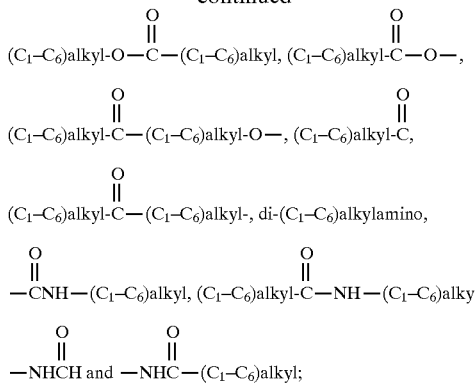

$R^5$ is hydrogen or a $C_1$–$C_6$-alkyl;

or $R^2$ and $R^5$, with the carbon atom to which they are bonded, form a saturated carbocyclic ring having from 3 to 7 carbon atoms in which one of said carbon atoms can optionally be replaced with oxygen, nitrogen or sulfur;

$R^3$ is an aryl selected from phenyl and naphthyl groups; a heteroaryl selected from indanyl, thienyl, furyl, pyridyl, thiazolyl, isothiazolyl, oxazolyl, isoxazolyl, triazolyl, tetrazolyl and quinolyl groups; or a $C_3$–$C_7$-cycloalkyl in which one of said carbon atoms can optionally be replaced with nitrogen, oxygen or sulfur; in said group $R^3$, each of said aryl and heteroaryl groups can optionally be substituted by one or more substituents and said $C_3$–$C_7$-cycloalkyl can optionally be substituted by one or two substituents, said substituents being independently selected from halogeno, nitro, $C_1$–$C_6$-alkyl, $C_1$–$C_6$-alkoxy, trifluoromethyl, amino, phenyl and ($C_1$–$C_6$)alkylamino groups and the following groups:

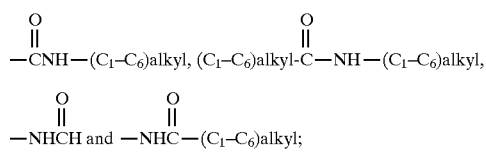

$R^4$ can be bonded to an atom of the nitrogen-containing ring which has an available bonding site and $R^7$ can be bonded to an atom of the ring containing $(CH_2)_z$ which has an available bonding site, and $R^4$, $R^6$, $R^7$ and $R^8$ are each independently selected from hydrogen, hydroxyl, halogeno, amino, carboxyl, carboxyalkyl, ($C_1$–$C_6$)alkylamino and di($C_1$–$C_6$)alkylamino groups, a $C_1$–C6-alkoxy, the following groups:

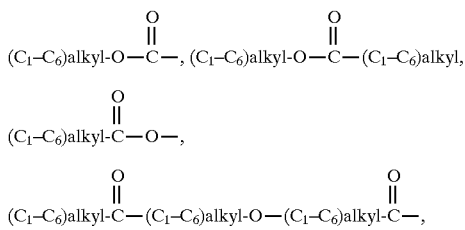

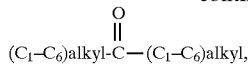

and the radicals indicated in the definition of $R^2$, with the proviso that (a) when m is 0, $R^8$ is absent, (b) neither $R^4$, nor $R^6$, nor $R^7$, nor $R^8$ can form a ring with the carbon atom to which it is bonded and with $R^5$, and (c) $R^4$ and $R^7$ cannot be bonded to the same carbon atom.

The thiopyranopyrrole derivatives of formula XXI and their pharmaceutically acceptable salts described in patent application WO92/20685 are also $NK_1$ receptor antagonists which are useful according to the present invention:

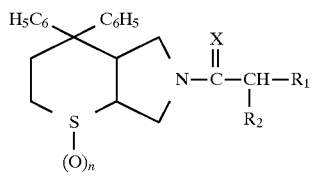

in which:

X is an oxygen atom or an NH radical;

$R_1$ is a phenyl radical optionally substituted by one or more halogen atoms, hydroxyl radicals, alkyl radicals which can optionally be substituted (by halogen atoms or amino, alkylamino or dialkylamino radicals) or alkoxy or alkylthio radicals which can optionally be substituted [by hydroxyl, amino, alkylamino or dialkylamino radicals optionally substituted (by phenyl, hydroxyl or amino radicals) or dialkylamino radicals of which the alkyl moieties form, with the nitrogen atom to which they are attached, a 5- or 6-membered heterocycle which can contain another heteroatom selected from oxygen, sulfur and nitrogen, optionally substituted by an alkyl, hydroxyl or hydroxyalkyl radical], or substituted by amino radicals, alkylamino radicals or dialkylamino radicals of which the alkyl moieties can form, with the nitrogen atom to which they are attached, a heterocycle as defined above, or is a cyclohexadienyl or naphthyl radical or a saturated or unsaturated, monocyclic or polycyclic heterocyclyl radical containing 5 to 9 carbon atoms and one or more heteroatoms selected from oxygen, nitrogen and sulfur;

$R_2$ is a hydrogen or halogen atom or a hydroxyl, alkyl, aminoalkyl, alkylaminoalkyl, dialkylaminoalkyl, alkoxy, alkylthio, acyloxy, carboxyl, alkoxycarbonyl, dialkylaminoalkoxycarbonyl, benzyloxycarbonyl, amino, acylamino or alkoxy-carbonylamino radical; and n is an integer from 0 to 2;

the above-mentioned alkyl and acyl radicals being linear or branched and containing 1 to 4 carbon atoms.

The compounds of formula XXII and their acceptable pharmaceutical salts described in WO93/01170 are also $NK_1$ receptor antagonists which are useful according to the present invention:

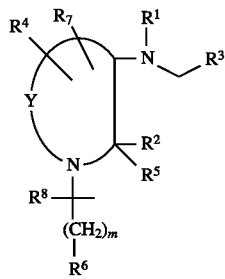

in which:

Y is $(CH_2)_n$, in which n is an integer from 1 to 6, in which one of the carbon-carbon single bonds of said $(CH_2)_n$ can optionally be replaced with a carbon-carbon double bond, in which one of the carbon atoms of said $(CH_2)_n$ can optionally be substituted by $R^4$, and in which any one of the carbon atoms of said $(CH_2)_n$ can optionally be substituted by $R^7$;

m is an integer from 0 to 8, one of the carbon-carbon single bonds of said $(CH_2)_m$ can optionally be replaced with a carbon-carbon double bond, and one of the carbon atoms of said $(CH_2)_m$ can optionally be substituted by $R^8$;

$R^1$ is hydrogen or a $C_1$–$C_6$-alkyl optionally substituted by a hydroxyl, alkoxy or fluoro group;

$R^2$ is a radical selected from hydrogen, a linear or branched $C_1$–$C_6$-alkyl, a $C_3$–$C_7$-cycloalkyl in which one of the carbon atoms can optionally be replaced with nitrogen, oxygen or sulfur; an aryl selected from a phenyl and a naphthyl; a heteroaryl selected from an indanyl, a thienyl, a furyl, a pyridyl, a thiazolyl, an isothiazolyl, an oxazolyl, an isoxazolyl, a triazolyl, a tetrazolyl and a quinolyl, and a phenyl($C_2$–$C_6$)alkyl, a benzhydryl and a benzyl, in said group $R^2$, each of said aryl and heteroaryl groups, and the phenyl moieties of said benzyl, said phenyl($C_2$–$C_6$)alkyl and said benzhydryl, can optionally be substituted by one or more substituents independently selected from a halogeno, a nitro, a $C_1$–$C_6$-alkyl, a $C_1$–$C_6$-alkoxy, a trifluoromethyl, an amino, a ($C_1$–$C_6$)alkylamino and the following groups:

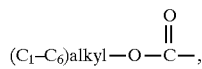

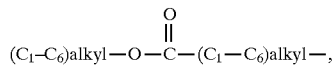

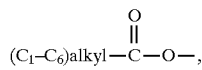

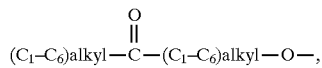

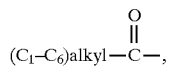

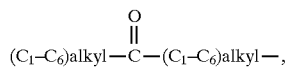

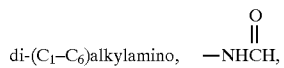

-continued

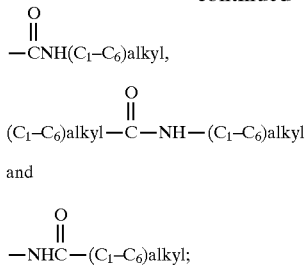

and

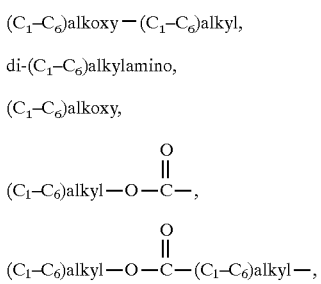

and in which one of the phenyl moieties of said benzhydryl can be replaced with naphthyl, thienyl, furyl or pyridyl;

$R^5$ is hydrogen, a phenyl group or a $C_1$–$C_6$-alkyl;

or $R^2$ and $R^5$, with the carbon atom to which they are bonded, form a saturated $C_3$–$C_7$ carbocyclic ring in which one of said carbon atoms can optionally be replaced with oxygen, nitrogen or sulfur;

$R^3$ is an aryl selected from phenyl and naphthyl groups, a heteroaryl selected from indanyl, thienyl, furyl, pyridyl, thiazolyl, isothiazolyl, oxazolyl, isoxazolyl, triazolyl, tetrazolyl and quinolyl groups, or a $C_3$–$C_7$-cycloalkyl in which one of said carbon atoms can optionally be replaced with nitrogen, oxygen or sulfur, in said group $R^3$, each of said aryl and heteroaryl groups can optionally be substituted by one or more substituents and said $C_3$–$C_7$-cycloalkyl can optionally be substituted by one or two substituents, said substituents being independently selected from halogeno, nitro, $C_1$–$C_6$-alkyl, $C_1$–$C_6$-alkoxy, methyl, trifluoromethyl, phenyl, amino and ($C_1$–$C_6$)-alkylamino groups and the following groups:

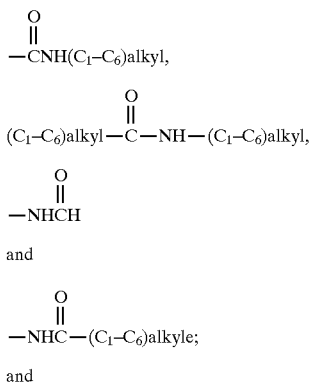

and and $R^4$ and $R^7$ are each independently selected from hydrogen, hydroxyl, halogeno, amino, oxo, nitro and ($C_1$–$C_6$)alkylamino groups, the following groups:

($C_1$–$C_6$)alkoxy—($C_1$–$C_6$)alkyl, di-($C_1$–$C_6$)alkylamino, ($C_1$–$C_6$)alkoxy, ($C_1$–$C_6$)alkyl—O—C(=O)—, ($C_1$–$C_6$)alkyl—O—C(=O)—($C_1$–$C_6$)alkyl—, hydroxy-($C_1$–$C_6$)alkyl,

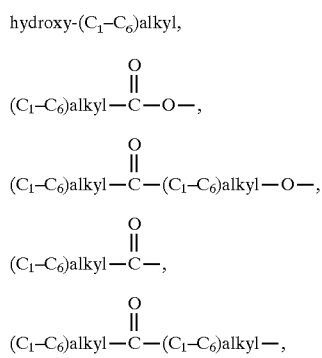

and the radicals indicated previously definition of $R^2$; $R^6$ is:

or one of the radicals given above in one of the definitions of $R^2$, $R^4$ and $R^7$;

$R^8$ is an oximino (=NOH) or one of the radicals given above in one of the definitions of $R^2$, $R^4$ and $R^7$; and $R^9$ is a ($C_1$–$C_6$)alkyl, hydrogen, a phenyl or a phenyl ($C_1$–$C_6$)alkyl; with the proviso that (a) when m is 0, $R^8$ is absent, (b) neither $R^4$, nor $R^6$, nor $R^7$, nor $R^8$ can form a ring with the carbon atom to which it is bonded and with $R^5$, (c) when $R^4$ and $R^7$ are bonded to the same carbon atom, then either each radical $R^4$ and $R^7$ is independently selected from hydrogen, a fluoro group and a $C_1$–$C_6$-alkyl, or $R^4$ and $R^7$, with the carbon atom to which they are bonded, form a saturated $C_3$–$C_6$ carbocyclic ring which forms a spiro compound with the nitrogen-containing ring to which they are bonded, (d) when n is 2 and either $R^4$ or $R^7$ is a hydroxy($C_1$–$C_6$) alkyl or 5-($C_1$–$C_6$)alkoxy($C_1$–$C_6$)alkyl group, then the other group $R_4$ or $R_7$ is hydrogen, (e) when n is 2, neither $R_4$ nor $R_7$ is a 4-hydroxy($C_1$–$C_6$)alkyl or 4-($C_1$–$C_6$)alkoxy($C_1$–$C_6$)alkyl group, and (f) in all the compounds of formula (XXII), either $R^3$ is a substituted aryl with at least one phenyl group, or one or both of the groups $R_4$ and $R_7$ are a hydroxy($C_1$–$C_6$)alkyl or ($C_1$–$C_6$)alkoxy($C_1$–$C_6$)alkyl group.

The perhydroisoindole derivatives of formulae XXIIIa and XXIIIb and their pharmaceutically acceptable salts described in patent application WO93/21155 are also $NK_1$ receptor antagonists which are useful according to the present invention:

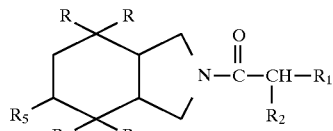
XXIIIa

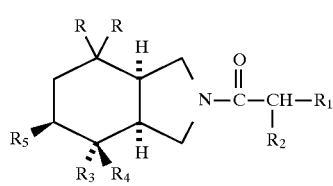
XXIIIb in which:

R is a phenyl radical optionally substituted by a halogen atom or by a methyl radical in the 2- or 3-position;

$R_1$ is a phenyl radical optionally substituted by one or more halogen atoms, hydroxyl radicals, alkyl radicals which can optionally be substituted (by halogen atoms or amino, alkylamino or dialkylamino radicals) or alkoxy or alkylthio radicals which can optionally be substituted [by hydroxyl, amino, alkylamino or dialkyamino radicals optionally substituted (by phenyl hydroxyl or amino radicals) or dialkylamino radicals of which the alkyl moieties form, with the nitrogen atom to which they are attached, a 5- or 6-membered heterocycle which can contain another heteroatom selected from oxygen, sulfur and nitrogen, optionally substituted by an alkyl, hydroxyl or hydroxyalkyl radical], or substituted by amino radicals, alkyl-amino radicals or dialkylamino radicals of which the alkyl moieties can form, with the nitrogen atom to which they are attached, a heterocycle as defined above, or is a cyclohexadienyl, naphthyl or indenyl radical or a saturated or unsaturated, monocyclic or polycyclic heterocyclyl radical containing 5 to 9 carbon atoms and one or more heteroatoms selected from oxygen, nitrogen and sulfur, and optionally substituted by a halogen atom or by an alkyl or alkoxy radical;

$R_2$ is a hydrogen or halogen atom or a hydroxyl, alkyl, aminoalkyl, alkylamino-alkyl, dialkylaminoalkyl, alkoxy, alkylthio, acyloxy, carboxyl, alkoxycarbonyl, dialkylaminoalkoxycarbonyl, benzyloxycarbonyl, amino or acylamino radical, $R_3$ is a phenyl radical optionally substituted in the 2-position by an alkyl or alkoxy radical containing 1 or 2 carbon atoms;

$R_4$ is a fluorine atom or a hydroxyl radical; and $R_5$ is a hydrogen atom; or $R_4$ and $R_5$ are hydroxyl radicals; or $R_4$ forms a bond with $R_5$;

the above-mentioned alkyl and acyl radicals being linear or branched and containing, 1 to 4 carbon atoms (unless indicated otherwise).

The compounds of formula XXIV and their pharmaceutically acceptable salts described in patent application WO94/04487 are also $NK_1$ receptor antagonists which are useful according to the present invention:

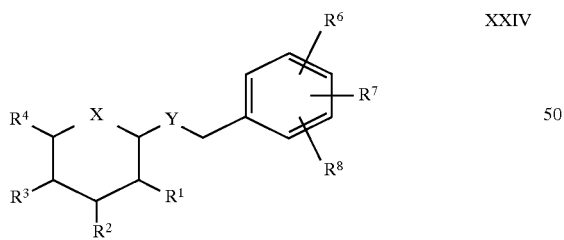

XXIV in which:

$R^1$ is selected from the following groups:
(1) phenyl which is unsubstituted or substituted by one or more substituents $R^{11}$, $R^{12}$ and $R^{13}$, where $R^{11}$, $R^{12}$ and $R^{13}$ are as defined below;
(2) $C_1$–$C_8$-alkyl which is unsubstituted or substituted by one or more substituents selected from the following groups:
(a) hydroxyl, (b) oxo, (c) $C_1$–$C_6$-alkoxy, (d) phenyl $(C_1$–$C_3)$alkoxy, (e) phenyl, (f) —CN, (g) halogeno, (h) —$NR^9R^{10}$, in which $R^9$ and $R^{10}$ are independently selected from:

(i) hydrogen, (ii) a phenyl, (iii) a $C_1$–$C_6$-alkyl which is unsubstituted or substituted by one or more substituents selected from the following groups:
(A) hydroxyl, (B) oxo, (C) $C_1$–$C_6$-alkoxy, (D) phenyl($C_1$–$C_3$)alkoxy, (E) phenyl, (F) —CN, (G) halogeno, (H) —$NR^{14}R^{15}$, in which $R^{14}$ and $R^{15}$ are independently selected from hydrogen, a $C_1$–$C_6$-alkyl, a phenyl and —$CO_2$— $(C_1$–$C_6)$alkyl, (I) -heterocycle, in which the heteroaryl is selected from the following groups:
(a) benzimidazolyl, (b) benzofuranyl, (c) benzothiophenyl, (d) benzoxazolyl, (e) furanyl, (f) imidazolyl, (g) indolyl, (h) isoxazolyl, (i) isothiazolyl, (j) oxadiazolyl, (k) oxazolyl, (l) pyrazinyl, (m) pyrazolyl, (n) pyridyl, (o) pyrimidyl, (p) pyrrolyl, (q) quinolyl, (r) tetrazolyl, (s) thiadiazolyl, (t) thiazolyl, (u) thienyl, (v) triazolyl, (w) azetidinyl, (x) 1,4-dioxanyl, (y) hexahydroazepinyl, (z) oxanyl, (aa) piperazinyl, (ab) piperidinyl, (ac) pyrrolidinyl, (ad) tetrahydrofuranyl and (ae) tetrahydrothienyl,
and in which the heterocycle is unsubstituted or substituted by one or more substituents selected from the following groups:
(i) $C_1$–$C_6$-alkyl which is unsubstituted or substituted by a halogeno, —$CF_3$, —$OCH_3$ or a phenyl, (ii) $C_1$–$C_6$-alkoxy, (iii) oxo, (iv) hydroxyl, (v) thioxo, (vi) —$SR^{14}$, (vii) halogeno, (viii) cyano, (ix) phenyl, (x) trifluoromethyl, (xi) —$(CH_2)_m$—$NR^{14}R^{15}$, in which m is equal to 0, 1 or 2, (xii) —$NR^{14}COR^{15}$, (xiii) —$CONR^{14}R^{15}$, (xiv) —$CO_2R^{14}$, (xv) —$(CH_2)_m$—$OR^{14}$,
(i) —$NR^9COR^{10}$, (j) —$NR^9CO_2R^{14}$, (k) —$NR^{14}CONR^9R^{10}$, (l) —$CONR^9R^{10}$, (m) —$COR^9$, (n) —$CO_2R^9$, (o) —$S(O)_n$—$R^9$; and (3) $R^9$, in which $R^9$ is as defined above, with the proviso that $R^9$ is not hydrogen or a phenyl;

$R^2$ is independently selected from:
(1) a $C_1$–$C_6$-alkyl which is unsubstituted or substituted by one or more substituents selected from groups of the following types:
(a) hydroxyl, (b) oxo, (c) $C_1$–$C_6$-alkoxy, (d) phenyl $(C_1$–$C_3)$alkoxy, (e) phenyl, (f) —CN, (g) halogeno, (h) —$NR^9R^{10}$, (i) —$NR^9COR^{10}$, (j) —$NR^9CO_2R^{10}$, (k) —$NR^{14}CONR^9R^{10}$, (l) —$CONR^9R^{10}$, (m) —$COR^9$, (n) —$CO_2R^9$, (o) —$S(O)$—$R^9$, in which n is equal to 0, 1 or 2;
(2) —$R^9$, with the proviso that $R^9$ is not hydrogen or a phenyl,
(3) —O—$R^9$, with the proviso that $R^9$ is not hydrogen or a phenyl; and
(4) —S—$R^9$, with the proviso that $R^9$ is not hydrogen or a phenyl;

$R^3$ and $R^4$ are chosen independently from:
(1) hydrogen;
(2) a $C_1$–$C_6$-alkyl which is unsubstituted or substituted by one or more substituents selected from groups of the following types:
(a) hydroxyl, (b) oxo, (c) $C_1$–$C_6$-alkoxy, (d) phenyl $(C_1$–$C_3)$alkoxy, (e) phenyl, (f) —CN, (g) halogeno, (h) —$NR^9R^{10}$, (i) —$NR^9COR^{10}$, (j) —$NR^9CO_2R^{10}$, (k) —$NR^{14}CONR^9R^{10}$, (l)

—CONR$^9$R$^{10}$, (m) —COR$^9$, (n) —CO$_2$R$^9$, (o) —S(O)$_n$—R$^9$; and (3) a phenyl which is unsubstituted or substituted by one or more radicals R$^6$, R$^7$ and R$^8$;

and the groups R$^3$ and R$^4$ can be joined together by a C$_1$–C$_4$-alkyl or a C$_1$–C$_4$-alkenyl to form a carbocyclic ring selected from the group consisting of:

(a) a cyclopentyl, (b) a cyclohexyl, (c) a phenyl, where the carbocyclic ring is unsubstituted or substituted by one or more substituents selected from groups of the following types:
(i) C$_1$–C$_6$-alkyl, (ii) C$_1$–C$_6$-alkoxy, (iii) —NR$^9$R$^{10}$, (iv) halogeno and (v) tri-fluoromethyl;

R$^6$, R$^7$ and R$^8$ are independently selected from the group consisting of:
(1) hydrogen;
(2) a C$_1$–C$_6$-alkyl which is unsubstituted or substituted by one or more substituents selected from groups of the following types:
(a) hydroxyl, (b) oxo, (c) C$_1$–C$_6$-alkoxy, (d) phenyl (C$_1$–C$_3$)alkoxy, (e) phenyl, (f) —CN, (g) halogeno, (h) —NR$^9$R$^{10}$, (i) —NR$^9$COR$^{10}$, (j) —NR$^9$CO$_2$R$^{10}$, (k) —NR$^{14}$CONR$^9$R$^{10}$, (l) —CONR$^9$R$^{10}$, (m) —COR$^9$, (n) —CO$_2$R$^9$, (o) —S(O)$_n$—R$^9$, in which n is equal to 0, 1 or 2;
(3) a C$_2$–C$_6$-alkenyl which is unsubstituted or substituted by one or more substituents selected from groups of the following types:
(a) hydroxyl, (b) oxo, (c) C$_1$–C$_6$-alkoxy, (d) phenyl (C$_1$–C$_3$)alkoxy, (e) phenyl, (f) —CN, (g) halogeno, (h) —CONR$^9$R$^{10}$, (i) —CO$_2$R$^9$, (j) —CO$_2$R$^9$;
(4) a C$_2$–C$_6$-alkenyl;
(5) a phenyl which is unsubstituted or substituted by one or more substituents selected from groups of the following types:
(a) hydroxyl, (b) C$_1$–C$_6$-alkoxy, (c) C$_1$–C$_6$-alkyl, (d) C$_2$–C$_5$-alkenyl, (e) halogeno, (f) —CN, (g) —NO$_2$, (h) —CF$_3$, (i) —(CH$_2$)$_n$-NR$^9$R$^{10}$, (j) —NR9COR$^{10}$, (k) —NR$^9$CO$_2$R$^{10}$, (l) —NR$^{14}$CONR$^9$R$^{10}$, (m) —CONR$^9$R$^{10}$, (n) —COR$^9$, (o) —CO$_2$R$^9$, (p) —S(O)$_n$—R$^9$, in which n is equal to 0, 1 or 2;
(6) a halogeno; (7) —CN; (8) —CF$_3$; (9) —OCF$_3$; (10) —NO$_2$; (11) a hydroxyl; (12) a C$_1$–C$_6$-alkoxy; (13) —COR$^9$; (14) —CO$_2$R$^9$; (15) —CONR$^9$COR$^{10}$; (16) —SR$^{14}$; (17) —SOR$^{14}$; (18) —SO$_2$R$^{14}$; (19) —NR$^9$R$^{10}$, (20) —NR$^9$COR$^{10}$; (21) —NR$^9$CO$_2$R$^{10}$; and 22) —NR$^{14}$CONR$^9$R$^{10}$;

R$^{11}$, R$^{12}$ and R$^{13}$ are independently selected from the definitions of R$^6$, R$^7$ and R$^8$;

X is:
(1) —CH(R$^5$)—, in which R$^5$ is independently selected from the definitions of R$^9$ and R$^{10}$; or
(2) a C$_2$–C$_3$-alkyl which is unsubstituted or substituted by R$^5$, R$^5$ being as defined above; and Y is selected from the group consisting of
(1) —O—, (2) —S—, (3) —N(R$^9$)—, (4) —N(COR$^9$)—, (5) —N(CO$_2$R$^9$)-, (6) —N(CONR$^9$R$^{10}$)-, in the definitions of R$_1$, R$_2$, R$^3$, R$^4$, R$^6$, R$_7$ and R$^8$, the radicals R$^9$, R$^{16}$, R$^{14}$ and R$^{15}$ are as defined above.

The invention further relates to the use of the enantiomers of the compounds defined above, where they exist.

A group of NK$_1$ receptor antagonists which is particularly preferred for the purposes of the invention consists of the compounds of formula A below:

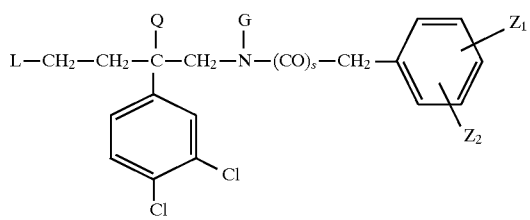

in which:

L is one of the following groups:

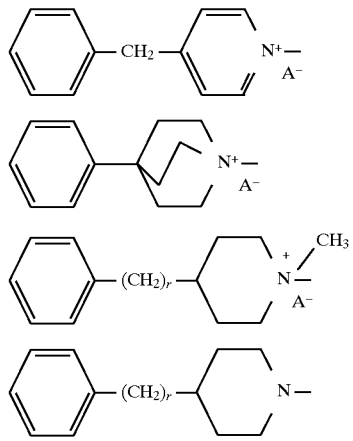

A is a pharmaceutically acceptable anion, preferably a chloride, methanesulfonate, benzenesulfonate or p-toluenesulfonate ion, Q is hydrogen and G is a C$_1$–C$_4$-alkyl group, or Q and G together form a group (CH$_2$)$_3$ or CH$_2$CH$_2$CO;

Z$_1$ and Z$_2$ independently of one another are a halogen, a (C$_1$–C$_4$)alkoxy group or the trifluoromethyl group; and r and s are 0 or 1, with the proviso that s is zero only when Q+G is CH$_2$CH$_2$CO; and their possible pharmaceutically acceptable salts.

The compound which is particularly preferred for the purposes of the invention is the compound SR 140333 cited previously. The compound of the formula

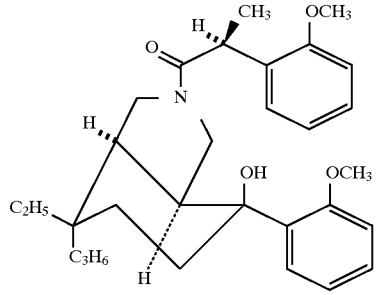

with the reference number RPR 100893 is also a preferred compound.

The cardioregulatory activity according to the present invention was demonstrated with a test on the rat by the method described in the Example below:

The compounds tested in this experiment, at doses of 0.5 μg/kg i.v., cause regulation of the heart rhythm.

NK$_1$ antagonists can be used to prepare drugs for preventing or controlling the pathological consequences of stress, especially in the cardiovascular system. The compounds according to the invention can also be used in association with other therapeutic agents which have a cardiovascular activity by different mechanisms of action.

By virtue of the discovery of this activity, $NK_1$ receptor antagonists can be used to prepare cardioregulatory drugs for normalizing the heart rate and rhythm. The compounds according to the present invention can optionally be used in association with other cardioregulatory agents which act by different mechanisms of action.

For their use as drugs according to the invention, $NK_1$ receptor antagonists must be formulated as pharmaceutical compositions.

In the pharmaceutical compositions of the present invention for oral, sublingual, subcutaneous, intramuscular, intravenous, topical, transdermal or rectal administration, the active principle can be administered to animals and humans in the form of unit doses, mixed with conventional pharmaceutical carriers, for the treatment of the above-mentioned complaints. The appropriate unit doses include doses for oral administration, such as tablets, which may be divisible, gelatin capsules, powders, granules and solutions or suspensions to be taken orally, doses for sublingual and buccal administration, doses for subcutaneous, intramuscular or intravenous administration and doses for rectal administration.

When a solid composition in the form of tablets is prepared, the main active ingredient is mixed with a pharmaceutical vehicle such as gelatin, starch, lactose, magnesium stearate, talcum, gum arabic or the like. The tablets can be coated with sucrose or other appropriate substances or else they can be treated so as to have a prolonged or delayed activity and so as to release a predetermined amount of active principle continuously.

A preparation in the form of gelatin capsules is obtained by mixing the active ingredient with a diluent and pouring the mixture obtained into soft or hard gelatin capsules.

A preparation in the form of a syrup or elixir can contain the active ingredient together with a sweetener, which is preferably calorie-free, methylparaben and propylparaben as antiseptics, a flavoring and an appropriate colorant.

The water-dispersible granules or powders can contain the active ingredient mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, saline solutions or sterile and injectable solutions which contain pharmacologically compatible dispersants and/or wetting agents, for example propylene glycol or butylene glycol.

The active principle can also be formulated as microcapsules, with one or more carriers or additives if appropriate.

In the pharmaceutical compositions according to the present invention, the active principle can also be in the form of an inclusion complex in cyclodextrins, their ethers or their esters.

To obtain the cardioregulatory effect, the dose of active principle can vary between 0.5 and 4000 mg per day, preferably between 2.5 and 1000 mg, depending on the weight and age of the patient and the severity of the complaints to be treated.

Each unit dose can contain from 0.5 to 1000 mg of active principle, preferably from 2.5 to 250 mg; this unit dose can be administered 1 to 4 times a day.

The invention will now be illustrated in greater detail by the non-limiting Example below.

EXAMPLE

The cardioregulatory activity of a representative compound of the invention (SR 140333) was determined by the method described below.

1. Physiological preparation

Fifteen Sprague-Dawley male rats weighing 250–350 g (Iffa-Credo, France) were anesthetized with urethane (1.25 g/kg i.p.) and placed in stereotaxic confinement. The lateral vein of the tail was catheterized to allow the injection of the test compound or its vehicle (distilled water+3 drops of Tween 80, 1 ml/kg i.v.). The heart rate was recorded by means of two metal electrodes inserted in the subcutaneous tissue on either side of the thoracic cavity. The signal was amplified, filtered and transformed by means of a TTL (Transistor Transistor Logic) pulse window discriminator according to the standard defined by the International Electrotechnical Commission and recognized in the United States by the Electronic Industry Association. It is a binary signal (logic 0:0 volt, logic 1:5 volts). These pulses were processed in real time on a PC to produce rhythm histograms in pulses/min. The appropriate parameters were measured in delayed time on these histograms.

2. Experimental procedure

The spontaneous heart rhythm was recorded and was allowed to stabilize for 15 to 25 min before mechanical stimulations were started. These consisted in pinching a back paw with a calibrated spring clip (P≈50 psi) for a period of 3 s. Two to 4 pinches were delivered at intervals of 5 min before the intravenous administration of the product SR 140333 A or its vehicle. Once the injection had been given, the stimulations were applied every 10 minutes over a maximum period of 85 minutes.

3. Processing of the data

For each stimulation, the number of heart pulses was measured over the one-minute period preceding and the one-minute period following the start of the stimulation. In the pre-injection period, the variation in the number of pulses thus obtained for each stimulation was determined and compared with that of the periods preceding the stimulations; the mean of the resulting values was then calculated. In the post-injection period, only the variation in the rhythm relative to its prestimulation level was determined. This variation for the different post-injection times was compared with the mean of the variations for the pre-injection period.

4. Results

The results are summarized in Table I. The nociceptive mechanical stimulation applied by pinching the back paw caused a moderate but significant increase in heart rhythm, which exceeded the 3 seconds of the actual stimulation itself. When the vehicle was injected on its own, there was no difference in this increase for the successive stimulations. The injection of SR 140333 A (0.5 $\mu$g/kg i.v.) almost totally eliminated the heart response to the stimulation. This decrease remained statistically significant for more than one hour after the injection, during which time the response was observed to recover to a degree. The successive percentage inhibitions were 97, 96, 99, 96, 80, 66 and 48 for the post-injection times of 5, 15, 25, 35, 45, 55 and 65 minutes, respectively.

5. Conclusions

The results of the present study show that the selective $NK_1$ receptor antagonist SR 140333 A blocks the acceleration of the heart rhythm which is caused by nociceptive mechanical stimulation.

TABLE I

Effects of SR 140333 A on the heart response to nociceptive stimulation at a time of 5 minutes after administration

| | Baseline rhythm[a] | Pre-injection | 5 minutes post-injection | % inhibition[d] |
|---|---|---|---|---|
| | | Variation induced by stimulation[a] | | |
| vehicle only[b] | 503 ± 39 | +35 ± 9* | +37 ± 10* | −6 |
| SR 140333 A[bc] | 517 ± 35 | +67 ± 11* | +2 ± 1γ | 97 |

[a]in beats/minute
[b]the values indicate the mean ± SEM, n = 5 rats
[c]0.5 μg/kg i.v.
[d]post-injection-pre-injection
*significant increase (P < 0.05)/baseline rhythm
γsignificant decrease (P < 0.05)/pre-injection value
statistics: ANOVA + Dunnett test

We claim:

1. A method for controlling heart rate disorders in a patient in need thereof which comprises administering to the patient an effective amount for controlling heart rate disorders of NK$_1$ receptor antagonist having a formula

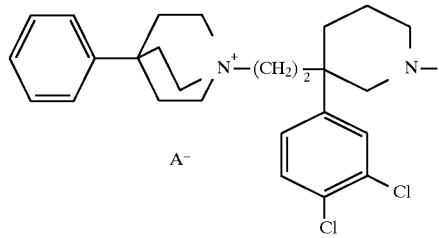

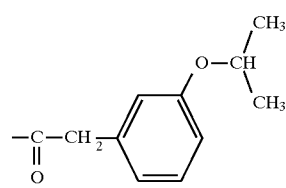

in which;

A is a pharmaceutically acceptable anion.

2. A method according to claim 1 wherein the pharmaceutically acceptable anion is chloride, benzenesulfonate, methanesulfonate or p-toluenesulfonate.

3. A method according to claim 1 preventing or controlling stress-related disorders.

4. A method according to claim 1 for preventing or controlling pain-related disorders.

5. A method according to claim 1, wherein the NK$_1$ receptor antagonist is the chloride or benzenesulfonate of (S)-1-{2-[3-(3,4-dichlorophenyl)-1-(3-]ethyl}-4-phenyl-1-azoniabicyclo-octane.

* * * * *